US009169302B2

(12) United States Patent
Carboulec et al.

(10) Patent No.: US 9,169,302 B2
(45) Date of Patent: Oct. 27, 2015

(54) HYPERBARIC DEVICE AND METHODS FOR PRODUCING INACTIVATED VACCINES AND FOR REFOLDING/SOLUBILIZING RECOMBINANT PROTEINS

(71) Applicants: Nicolas Pierre Yves Carboulec, Saint Goueno (FR); Gildas Merian, Bourg la reine (FR); Rene Labatut, Saint-Genis Laval (FR); Lionel Gerentes, Lyons (FR)

(72) Inventors: Nicolas Pierre Yves Carboulec, Saint Goueno (FR); Gildas Merian, Bourg la reine (FR); Rene Labatut, Saint-Genis Laval (FR); Lionel Gerentes, Lyons (FR)

(73) Assignees: MERIAL, INC., Duluth, GA (US); Top Industrie S.A.S. (FR)

( * ) Notice: Subject to any disclaimer, the term of this patent is extended or adjusted under 35 U.S.C. 154(b) by 0 days.

(21) Appl. No.: 14/014,434

(22) Filed: Aug. 30, 2013

(65) Prior Publication Data
US 2014/0065187 A1   Mar. 6, 2014

Related U.S. Application Data

(60) Provisional application No. 61/694,968, filed on Aug. 30, 2012, provisional application No. 61/830,425, filed on Jun. 3, 2013.

(51) Int. Cl.
*A61L 2/00* (2006.01)
*C07K 14/245* (2006.01)
(Continued)

(52) U.S. Cl.
CPC .............. *C07K 14/245* (2013.01); *A23L 3/0155* (2013.01); *A61K 39/008* (2013.01);
(Continued)

(58) Field of Classification Search
CPC .................................... A61L 2/00; A61L 2/26
USPC .......................................... 422/297, 300, 307
See application file for complete search history.

(56) References Cited

U.S. PATENT DOCUMENTS 8,377,375 B2    2/2013  Anderle et al.
2002/0076347 A1  6/2002  Maerz
(Continued)

FOREIGN PATENT DOCUMENTS

WO    WO 02/056824 A2    7/2002
WO    WO 04/000451 A2    12/2003
(Continued)

OTHER PUBLICATIONS

Hernando S et al: "Advances in design for successful commercial high pressure food processing", 1,2,5-7 Food Australia, North Sydney, AU, vol. 60, No. 4, Apr. 1, 2008, pp. 154-156, XP009175699.
(Continued)

*Primary Examiner* — Monzer R Chorbaji
(74) *Attorney, Agent, or Firm* — Judy Jarecki-Black; Chad Kitchen; Merial, Inc.

(57) ABSTRACT

The invention relates to hyperbaric devices for inactivating microorganisms and viruses while retaining their immunogenicity and for making and producing the soluble, disaggregated, refolded or active immunogenic or therapeutic proteins from inclusion bodies produced from prokaryotes or eukaryotes. The invention encompasses hyperbaric methods for inactivating pathogenic organisms, and methods for producing vaccine compositions using the inactivated pathogens. The hyperbarically inactivated microorganisms are safer and more immunogenic than chemically inactivated microorganisms. Similarly, the solubilized proteins have superior properties compared to more heavily aggregated proteins, including reduced non-specific immune reactions.

45 Claims, 28 Drawing Sheets

(51) Int. Cl.
*A23L 3/015* (2006.01)
*A61K 39/008* (2006.01)
*A61K 39/02* (2006.01)
*C12N 9/10* (2006.01)
*C12N 9/52* (2006.01)
*C07K 14/44* (2006.01)
*A61K 39/00* (2006.01)

(52) U.S. Cl.
CPC ........ *A61K 39/0225* (2013.01); *A61K 39/0241* (2013.01); *A61K 39/099* (2013.01); *A61L 2/0011* (2013.01); *C07K 14/44* (2013.01); *C12N 9/1007* (2013.01); *C12N 9/52* (2013.01); *A61K 2039/552* (2013.01); *C07K 2319/00* (2013.01)

(56) References Cited

U.S. PATENT DOCUMENTS

| | | |
|---|---|---|
| 2004/0038333 A1 | 2/2004 | Randolph et al. |
| 2008/0152775 A1 | 6/2008 | Paquin et al. |
| 2008/0161242 A1* | 7/2008 | Randolph et al. ............... 514/12 |
| 2008/0249286 A1 | 10/2008 | Seefeldt |
| 2009/0215998 A1 | 8/2009 | Antman et al. |
| 2010/0112660 A1 | 5/2010 | Rosendahl |
| 2011/0046357 A1 | 2/2011 | Randolph et al. |
| 2011/0070219 A1 | 3/2011 | Seefeldt et al. |
| 2012/0070406 A1 | 3/2012 | Seefeldt |
| 2014/0072594 A1 | 3/2014 | Fischer et al. |

FOREIGN PATENT DOCUMENTS

| | | |
|---|---|---|
| WO | WO 2009/111849 A1 | 9/2009 |
| WO | WO 2011/091860 A1 | 8/2011 |

OTHER PUBLICATIONS

Martin M F San et al: "Food processing by high hydrostatic pressure", Critical Reviews in Food Science and Nutrition, Taylor & Francis, USA, vo 1 . 42 , No. 6, Nov. 1, 2002, pp. 627-645, XP009175698.

Zimmerman F et al: "Isostatic High-Pressure Equipment for Food Preservation", Food Technology, Institute of Food Technologists, Chicago, IL, US, vol. 47, No. 6, Jun. 1, 1993, pp. 162-163, XP888372669.

Qoronfleh et al: "Confronting high-throughput protein refolding using high pressure and solution screens", Protein Expression and Purification, Academic Press, San Diego, CA, vol. 55, No. 2, Sep. 8 2887 (2887-89-88), pp. 289-224, XP822238126.

Brochure NC Hyperbaric 2007.

Cothran A. High-Pressure Refolding of Human Vascular Endothelial Growth Factor (VEGF) Recombinantly Expressed in Bacterial Inclusion Bodies: Refolding Optimization, and Feasibility Assessment. Biotechnol. Prog., 2011, vol. 27, No. 5.

Grzesiowski. Inactivation of Bacteria at High Pressure. Defect and Diffusion Forum Vols. 208-209 (2002) pp. 67-72.

Okai. High pressure refolding, purification, and crystallization of flavin reductase from Sulfolobus tokodaii strain 7. Protein Expression and Purification 84 (2012) 214-218.

Ritz M. Effects of high hydrostatic pressure on membrane proteins of Salmonella typhimurium. International J. Food Microbiology 55 (2000) 115-119.

Shearer A. High Hydrostatic Pressure for Development of Vaccines. J. Food Protection, vol. 72, No. 7, 2009, pp. 1500-1508.

Silva CCM. Effects of hydrostatic pressure on the Leptospira interrogans: high immunogenicity of the pressure-inactivated serovar hardjo. Vaccine 19 (2001) 1511-1514.

Silva CCM. Effects of Hydrostatic Pressure on a Membrane-Enveloped Virus: High Immunogenicity of the Pressure-Inactivated Virus. J. Virology, Apr. 1992, p. 2111- 2117.

Wuytak EY. Bacterial inactivation by high-pressure homogenization and high hydrostatic pressure. International Journal of Food Microbiology 77 (2002) 205-212.

Yan W. Immunogenicity and protective efficacy of recombinant Leptospira immunoglobulin-like protein B (rLigB) in a hamster challenge model. Microbes and Infection 11 (2009) 230-237.

Zheng H. Expression, high-pressure refolding and purification of human leukocyte cell-derived chemotaxin 2 (LECT2). Protein Expression and Purification 88 (2013) 221-229.

Isostat Prospekt GB 2004. Brochure.

* cited by examiner

Subjecting bacteria to specific conditions prevent "recovery phenomenon"

| Inactivation Conditions | Incubation Conditions | Inactivation After 11 Day Incubation |
|---|---|---|
| 60 min.<br>3500 bar<br>37°C | +5°C | + |
| | Ambient | + |
| | 37°C | + |
| 30 min.<br>4000 bar<br>37°C | +5°C | - |
| | Ambient | + |
| | 37°C | - |
| 90 min.<br>4000 bar<br>37°C | +5°C | - |
| | Ambient | - |
| | 37°C | - |

| Inactivation Conditions | Duration of Inactivation Stability | Incubation Conditions | Inactivation Control |
|---|---|---|---|
| 90 min.<br>4000 bars<br>37°C<br>20X | D0 | 37°C | - |
| | No Recovery<br>(D5, D10,<br>D17, D21) | +5°C | - |
| | | Ambient | - |
| | | 37°C | - |

*FIG. 16*

| Group | No. of Mice | Vaccine | Dilution | Protection Rate | ELISA Titer |
|---|---|---|---|---|---|
| 1 | 20 | Hyperbaric-inactivated | 1/25 | 100% | 3.35 |
| 2 | 20 | | 1/50 | 90% | 3.30 |
| 3 | 20 | | 1/100 | 50% | 3.09 |
| 4 | 20 | Formalin-inactivated | 1/25 | 90% | 3.42 |
| 5 | 20 | | 1/50 | 90% | 3.19 |
| 6 | 20 | | 1/100 | 20% | 2.76 |
| 7 | 20 | Merthiolate-inactivated | 1/25 | 90% | 3.49 |
| 8 | 20 | | 1/50 | 90% | 3.10 |
| 9 | 20 | | 1/100 | 60% | 2.81 |
| 10 | 10 | Not Vaccinated | - | 0% | - |

HYPERBARIC DEVICE AND METHODS FOR PRODUCING INACTIVATED VACCINES AND FOR REFOLDING/SOLUBILIZING RECOMBINANT PROTEINS

INCORPORATION BY REFERENCE

This application claims priority to U.S. provisional applications No. 61/694,968, filed on Aug. 30, 2012, and No. 61/830,425, filed on Jun. 3, 2013, both of which are herein incorporated by reference in their entirety. All documents cited or referenced herein, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to hyperbaric devices and to methods of using same to inactivate microorganisms and/or viruses for use in immunogenic/vaccine compositions, and to refold and/or solubilize recombinant proteins for use in therapeutic and immunogenic/vaccine compositions.

BACKGROUND OF THE INVENTION

Food scientists have long used hyperbaric conditions to reduce the microbial burden of foodstuffs. Vaccine biologists are also very interested in inactivating microorganisms, for their use in vaccine preparations. However, to make a safe, effective vaccine, one must 1) completely inactivate the pathogenic microorganism; and 2) retain the organism's immunogenic potential (immunogenicity). Before the instant invention was made, the skilled person knew certain combinations of pressure, temperature, and time could be used to reduce the number of viable microorganisms, however, he or she did not have a generally-applicable method to produce "vaccine-suitable" inactivated microorganisms. For examples of hyperbaric reduction of biological load in food, see e.g. Isbarn, 2007 (influenza); Ritz, 2000 (*salmonella*); and Wilkinson, 2001 (poliovirus). Up until recently, any retention of immunogenic potential by the microorganisms was merely incidental to the goal of reducing microbial burden.

As regards use of high pressure inactivation for vaccine production, one group achieved good inactivation of *Leptospira interrogans* serovar hardjo by subjecting the microorganisms to two kilobar for sixty minutes (Silva, 2001). The inactivated leptospires were able to elicit immune responses in rabbit, though their ability to elicit protective immune response in a target animal, such as a bovine, was not demonstrated. To date, Applicants are aware of no published results demonstrating complete protective immunity using pressure-inactivated bacteria or protozoal parasites. For a review, please see Shearer et al., 2009. In addition to not yet providing effective vaccines using hyperbaric inactivation methods, the field has yet to produce the necessary hyperbaric devices. Current high hydrostatic pressure (HHP) devices developed for merely reducing microbial burden lack the ability to completely inactivate pathogens and render them useful as vaccine constituents.

Moreover, existing hyperbaric methods introduce unacceptable, heterogeneous temperature distributions, which result in reduced yields for protein folding/solubilization and pathogen inactivation applications. Available devices affect pressure increases by using external pumps to inject additional liquid into a fixed-size vessel. Essentially, pumps outside the vessel pressurize the water, and as more water is injected into the vessel, the pressure increases, and an arrangement of valves maintains the desired pressure within the chamber. The temperature distribution problem stems from the pump because as one increases the pressure inside the pump, the water becomes very hot. Injecting the high pressure, hot water produces the high degree of temperature heterogeneity. These devices thus may be perfectly adequate for reducing pathogen burden in foodstuffs, where precision regulation of temperature and pressure is not required, but these devices cannot be efficiently applied to refold/solubilize protein or inactivate pathogens while maintaining their immunogenic potential. Companies working in this area include Barofold (see for example, U.S. Pat. Nos. 6,489,450, 7,064,192, 7,538,198, 7,767,795, 7,829,681, 8,329,878, and US20080161242A1) and Avure, which makes hyperbaric devices for the food processing industry.

As the prior art devices do not allow for optimal control over temperature and pressure, hyperbaric devices designed to provide precise control over these variables are required to serve facilitate immunogenicity-preserving pathogen inactivation and protein refolding/solubilization/solubilization.

Applicants have therefore developed specific hyperbaric methods and devices to produce vaccine-ready inactivated microorganisms and to refold/solubilize commercially relevant therapeutic and immunogenic proteins.

Citation or identification of any document in this application is not an admission that such document is available as prior art to the present invention.

SUMMARY OF THE INVENTION

The present disclosure concerns a hyperbaric device and methods of use thereof for 1) inactivating microorganisms while retaining their immunogenicity, and 2) the refolding/solubilization of recombinant proteins. Thus, a first object of the present disclosure is to provide a hyperbaric device for inactivating microorganisms and refolding/solubilizing proteins. Another object of the present disclosure is to provide methods for using the hyperbaric device to inactivate microorganisms and to refold/solubilize proteins. A third object of the disclosure is to provide immunogenic compositions comprising the hyperbaric-inactivated microorganisms; and a fourth object of the disclosure is to provide immunogenic and/or therapeutic proteins produced using the hyperbaric device.

The hyperbarically-inactivated microorganisms of the instant disclosure are ideally completely inactivated, while retaining their immunogenic potential, are safe, and are capable of eliciting protective immune responses in target animals, against virulent challenge. Similarly, the hyperbarically-produced immunogenic and/or therapeutic proteins are safe and effective when administered to human and non-human animals.

It is noted that in this disclosure and particularly in the claims, terms such as "comprises", "comprised", "comprising" and the likes can have the meaning attributed to them in U.S. Patent law; e.g., they can mean "includes", "included", "including", and the likes; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

The following Detailed Description, given by way of example, and not intended to limit the invention to specific embodiments described, may be understood in conjunction with the accompanying Figures, incorporated herein by reference, in which.

DETAILED DESCRIPTION OF THE INVENTION

Figure 1A:
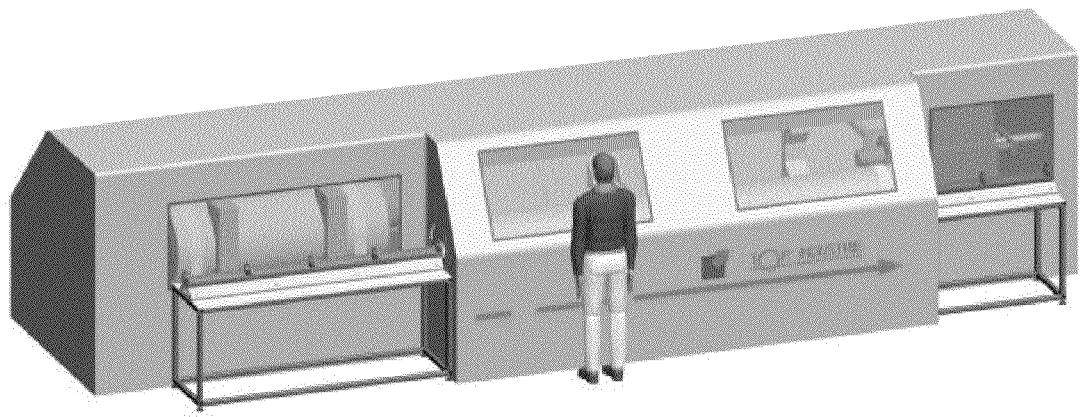
FIG. 1A depicts a hyperbaric device according to the invention.

The present disclosure concerns a hyperbaric device for 1) inactivating microorganisms while retaining their immunogenicity, and 2) the refolding/solubilization of recombinant proteins. Thus, a first object of the present disclosure is to provide a hyperbaric device for inactivating "microorganisms," (which, as used herein, are defined as bacteria, protozoans, any other single-celled eukaryotes, any other monerans, and viruses), while retaining their immunogenicity. Devices according to the instant disclosure may have a means for precisely controlling temperature and a means for precisely controlling pressure.

In an embodiment, the device has a means for receiving bags or other suitable containers, which are filled with microorganisms to be inactivated. The device may have incorporated therein a variety of means for sampling and assessing the inactivation status of the microorganisms. All functions of the device may be controlled via a suitable user interface and computer processing unit. In addition to inactivating microorganisms, the hyperbaric device may be effectively used in the refolding/solubilization of improperly folded and/or inclusion-body entrapped recombinant proteins. The disclosed device provides a significant advantage over previous technologies, in part, because it allows protein refolding and solubilization to be performed simultaneously.

The disclosure further relates to computer models and to methods of modeling temperature distribution within high pressure devices. Maintaining a uniform or homogeneous distribution of temperature is essential to demanding applications such as immunogenicity-preserving pathogen inactivation and protein refolding/solubilization. Precise temperature measurements were taken during operation of existing high pressure devices, and these data points were used to develop a temperature distribution model, which was validated against actual measurements taken from existing machines operating under various conditions of temperature and pressure. In brief, the model accurately predicted the temperature distribution within existing vessels, and so the model was applied to design a high pressure device capable of minimizing temperature distribution heterogeneity. Thus in an embodiment, the disclosed devices are free of unacceptable temperature variation.

The temperature distribution model guided selection of dimensional parameters, including tube length, thickness, and the like, with the goal of minimizing temperature variation within the high pressure chamber. Unlike the prior art fixed-size hyperbaric chambers, the instant disclosure provides a hyperbaric piston press device, wherein the high pressure chamber size is not constant, owing to the extension and retraction of the ram or piston press. The chamber size thus decreases with increasing pressure, and increases with decreasing pressure.

In an embodiment, devices according to the present disclosure contain a piston and seal arrangement to communicate pressure to fluid, including water, to a high pressure chamber. The increased pressure overcomes the intermolecular (e.g. $H_2O$ to $H_2O$) repulsion forces, and at 6000 bar, the water volume is reduced by approximately ten percent, relative to ambient pressure conditions. The device of the disclosure is particularly useful for inactivating pathogens because the highly controllable temperature and pressure can be used to stabilize proteins in their native state (i.e. good for preserving immunogenicity), while destroying/blocking enzymatic activities long enough to render the pathogens non-infective. In a particularly embodiment, the microorganisms or pathogens never recover from the initial hyperbaric-mediated molecular damage.

Likewise, the precise tuning of pressure and temperature can be used to facilitate protein refolding/solubilization. A protein has a specific molecular volume, which is determined by its three-dimensional structure, which is a function of its inherent amino acid content, its secondary structures, and the interplay of many forces, including van der waals and electrostatic interactions, hydrophobic interactions, hydrogen bonding, disulfide linkages, temperature, pressure, and the like. When a protein is misfolded, its specific volume is typically larger than when the same protein is properly folded. In an embodiment, pressure is precisely applied to facilitate protein folding, resulting in a reduction of the protein's specific volume.

As used herein, "properly folded" means the protein is in it native configuration, which is the configuration most associated with or attributed to the protein when it is competent to serve its primary structural and/or functional role. For example, a cell-membrane receptor is in it native configuration when it is capable of interacting with its cognate ligand(s) to engage in cell signaling activities. Similarly, an enzyme is in its native configuration when it is capable of interacting with and catalyzing the relevant reactions with its cognate substrate(s).

In an embodiment, controlled protein refolding/solubilization is achieved by first applying pressure to restrict the unfolded protein's freedom of movement (e.g. molecular vibration and rotation). However, decreasing the pressure too quickly can restrict movement so much that the protein cannot assume its native (properly folded) configuration. Therefore, devices according to the disclosure must be able to carefully control pressure, and the rate at which pressure is changed (and thus applied to the biological samples), to allow 1) an initial determination of ideal/optimal refolding/solubilization conditions; and 2) execution of said conditions to equivalent samples in the future.

In another embodiment, temperature can be increased to increase motion and energy (e.g. Brownian motion, intramolecular vibration, or interatomic motion), to reduce the time it takes for the misfolded protein to assume its native configuration.

In preferred embodiments, precise combinations of temperature and pressure conditions are determined for each type of biological sample to minimize the amount of time required to produce the maximum percentage of properly folded proteins.

In another embodiment, the device is advantageous over prior hyperbaric devices in that it provides for controlled decreases in pressure, and for holding at constant pressures. Proteins subjected to these controlled pressure conditions are more likely to efficiently refold to their native configurations, as compared to proteins subjected to rapid and uncontrolled decreases in pressure (i.e. the uncontrolled pressure reduction imparts excessive energy to the proteins, allowing them to move or jump to energetically stable, yet non-native configurations).

In several embodiments, the disclosed hyperbaric device comprises a piston and cylinder arrangement, which reduces or eliminates the amount of unwanted improper refolding/solubilization by allowing the pressure decreases to be precisely tuned and controlled.

In an embodiment, the device is advantageous in that it can be conveniently and rapidly de-contaminated. In a particular embodiment, the device is fully GMP-compliant, can be opened from both sides, and can be cleaned by any reasonably method including but not limited to steam cleaning.

The present disclosure thus provides a piston press hyperbaric device, which allows precise control and management of pressure and temperature to determine (and then provide) the optimal balance of pressure and temperature to obtain maximal protein refolding/solubilization and hence, yield.

These same properties allow the device to also optimize and apply effective combinations of pressure and temperature to inactivate microorganisms/pathogens while retaining their immunogenic potential. In some embodiments, the hyperbaric device improves the immunogenic potential of the microorganisms it inactivates.

In an embodiment, the disclosure provides an enclosure for housing the hyperbaric device (see FIG. 1A). The enclosure is designed to take into account both the constraints of high pressure and ease of cleaning/de-contamination. The enclosure may accommodate any commercially useful volume and pressure conditions, including, but not solely, up to 4,000 bar, up to 5,000 bar, up to 6,000 bar, up to 7,000 bar, up to 8,000 bar, up to 9,000 bar, or up to about 10,000 bar. Useful operating volumes include, for example, 50 liters or more.

In an embodiment the inactivation device housed within the enclosure may comprise two cylinders enclosed in a metal frame. The device may assume any useful configuration in accordance with this disclosure, and may take the general form depicted in FIGS. 2A, 2B, 3, and 4.

Figure 2A:
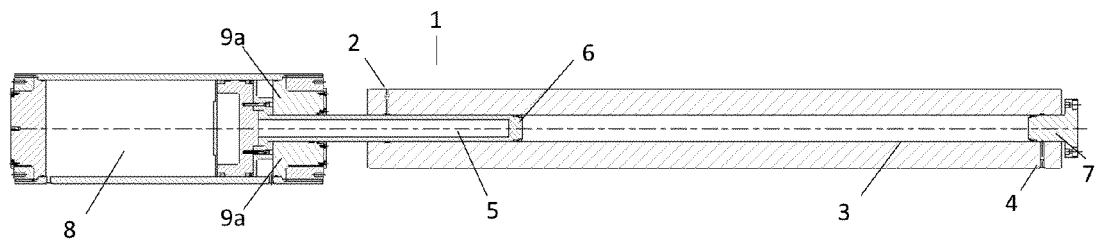
FIG. 2A depicts a hyperbaric press assembly (1) for communicating pressure to samples. Fluid enters the high pressure fluid chamber (3) via inlet (2) while pressure ram/piston (5) is retracted. The ram (5) then extends into the depicted position, and seal (6) and plug (7) prevent the fluid from escaping the high pressure fluid chamber (3). After completion of the pressurization and depressurization cycle(s), fluid is discharged via outlet (4). Pressure is communicated to the primary fluid chamber (8) via the pressure intensifier chamber (9), which receives high pressure air/fluid from a pressure intensifier device. Pressure in the primary fluid chamber (8) is communicated to the high pressure fluid chamber (3) via the ram (5)
Figure 2B:
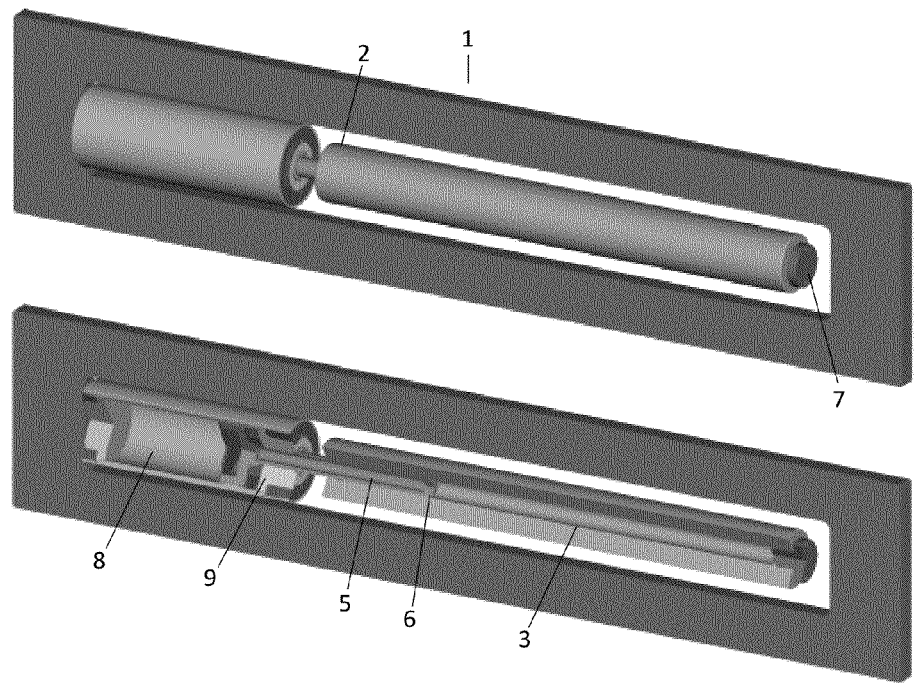
FIG. 2B is a three dimensional rendering of a press (1) according to the disclosure.

In an embodiment, such as that depicted in FIG. 2A, the hyperbaric device comprises a press assembly (1) for communicating pressure to samples. Fluid enters the high pressure fluid chamber (3) via inlet (4) while pressure intensifier ram (5) is retracted. The ram (5) then extends into the depicted position, and ram high pressure seals (6) and high pressure plug (7) prevent the fluid from escaping the high pressure fluid chamber (3). After completion of the pressurization and depressurization cycle(s), fluid is discharged via outlet (2). Pressure is communicated to the primary fluid chamber (8) via the upper chamber of the intensifier (9). Pressure in the primary fluid chamber (8) is communicated to the high pressure fluid chamber (3) via the ram (5).

Figure 3:
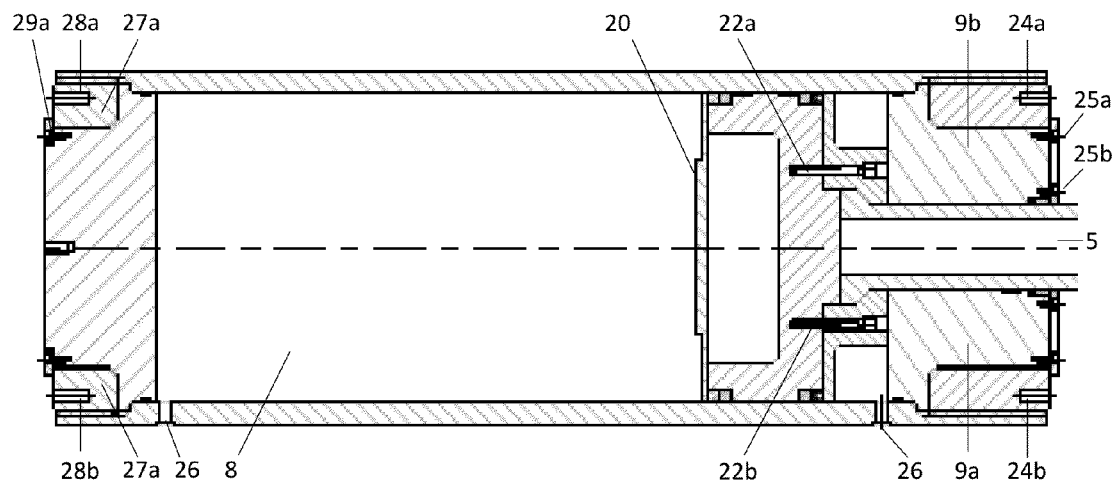
FIG. 3 is an enlarged version of the press assembly (1), focused on the primary fluid chamber (8). Various components are labeled and further described in the detailed description section below.
Figure 4:
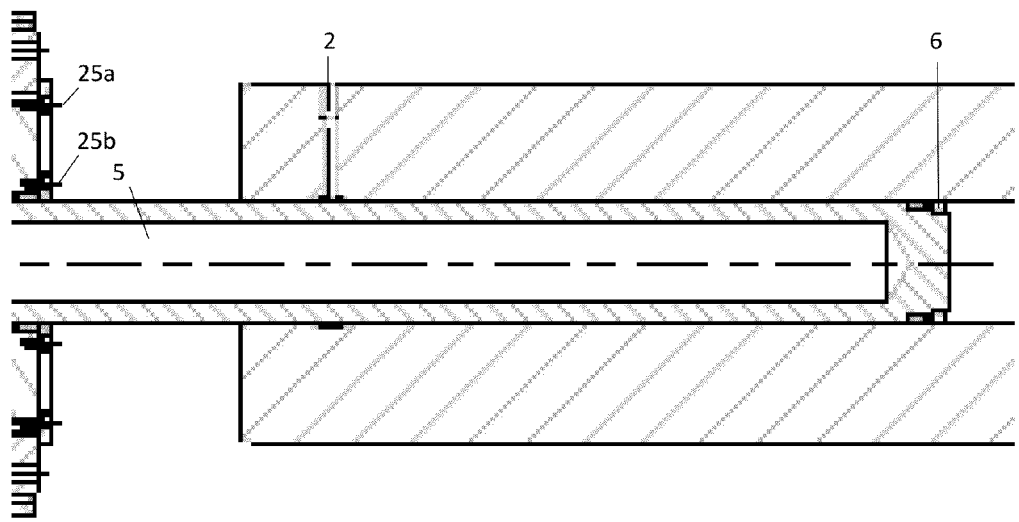
FIG. 4 is an enlarged version of the press assembly (1), focused on the ram (5). Various components are labeled and further described below.
Figure 5:
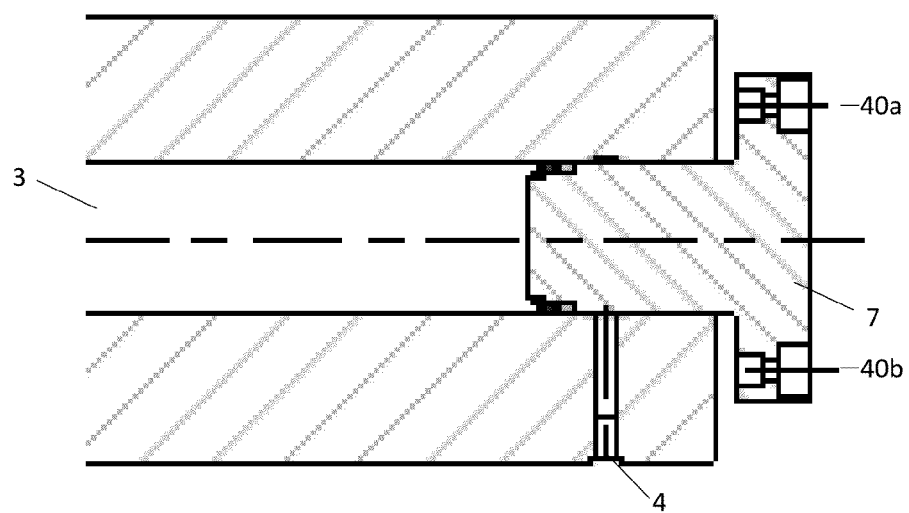
FIG. 5 is an enlarged version of the press assembly (1), focused on the plug (7). Various components are labeled and further described below.
Figure 6:
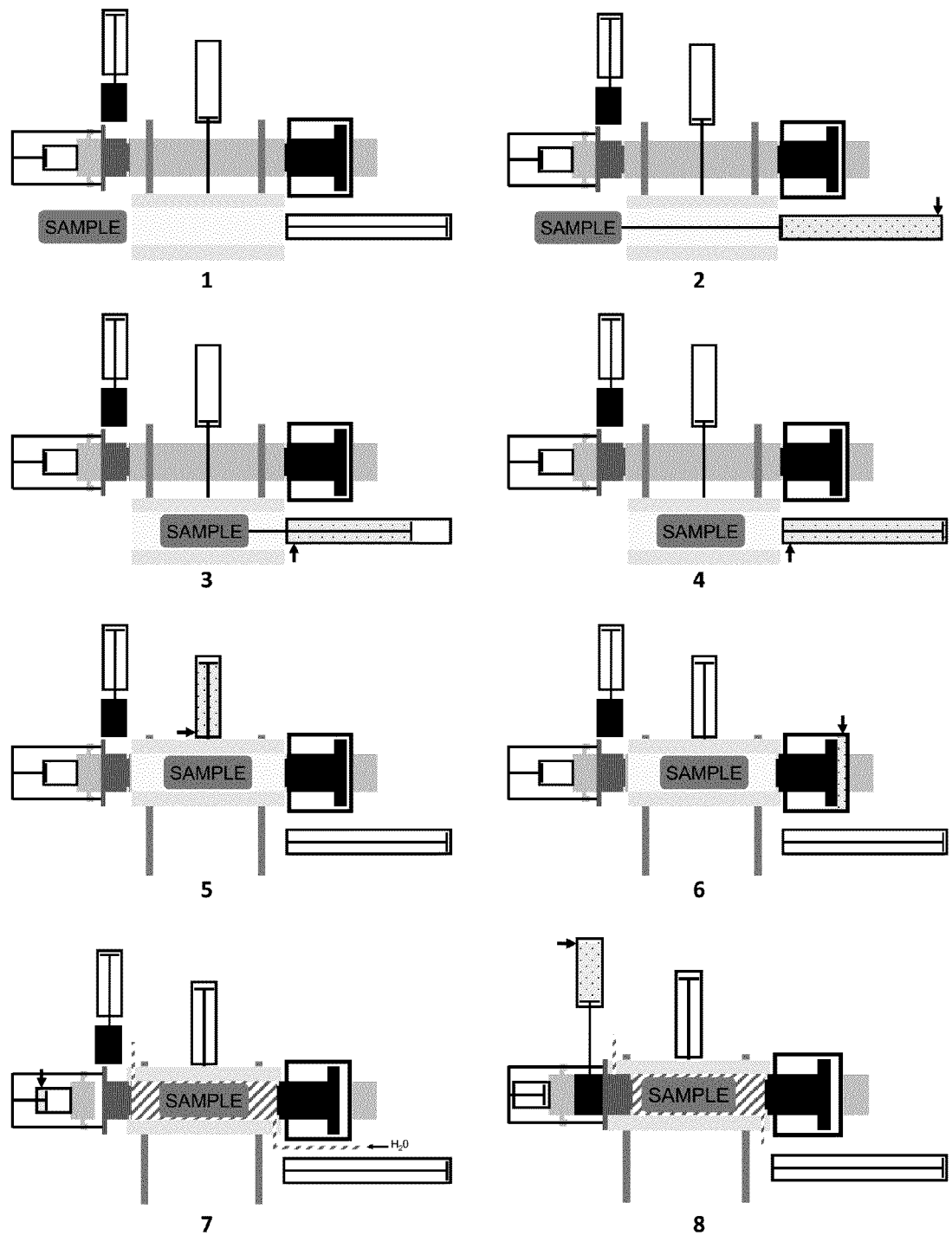
FIG. 6 is a schematic representation of a hyperbaric device, according to the instant disclosure, performing a cycle of pressurization/depressurization on a sample containing pathogens to be inactivated or peptides to be refolded and/or solubilized from bacterial inclusion bodies. 1) Product in chamber, ready to be loaded; 2) extension of charging cylinder; 3) removal of sample from holding chamber; 4) retraction of the loading cylinder; 5) positioning of sample into enclosure; 6) cylinder advances to make a seal, enabling pressure multiplier filling; 7) left cylinder advances for filling; 8) left cylinder advances further to seal the chamber; 9) implementation of the block, which prevents the left cylinder from retracting; 10) right cylinder extended further to the left to increase pressure; 11) pressure released; 12) block withdrawn; 13) left cylinder withdrawn for draining; 14) starting position for pressure multiplier; 15) extend body to unload sample; 16) extend charging cylinder.
Figure 6:
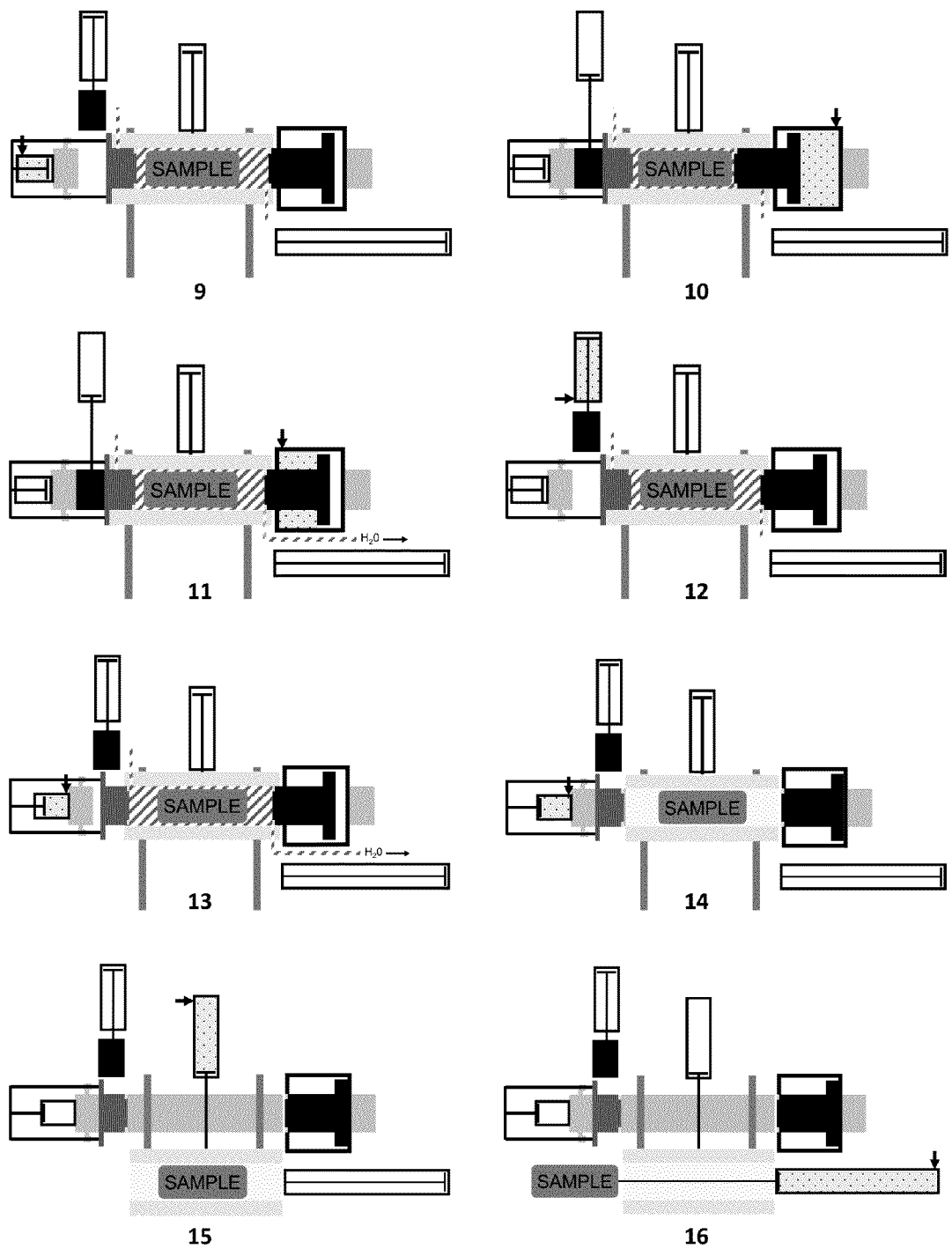

In an embodiment, the press assembly may include components as illustrated in the magnified views of FIGS. 3-5. The assembly may include: a seal holding plate (20); main ram holding screws (22a & b); an upper chamber holder dismantling device (24a & b); an upper chamber dismantling device (25a); an upper chamber seal (25b); a primary fluid input (26); a lower chamber holder (27a); a lower chamber holder dismantling device; and a lower chamber dismantling device (29a).

In an embodiment, the metal frame may be loaded to absorb the thrust of the piston chamber and the multiplier so that these two elements remain fixed despite the forces generated by the pressure.

In a particular embodiment, a compact design minimizes spread of contamination, in the event of a breach, particularly when compared to a more open design requiring a group of independent and external sources of pressure. In addition, the compact design avoids the need for a series of high pressure pipes, which would necessitate the frequent replacement of numerous valves, which is undesirable in a contaminable area.

In an embodiment, the pressure intensifier and the piston may be separated from the enclosure to allow easy access to the interior of the enclosure and easy changing of piston seals in the event of contamination. The pressure multiplier may preferably accommodate longer run times, for example, up to about 10 hours, 11 hours, 12 hours, 13 hours, 14 hours, 15 hours, 16 hours, 17 hours, 18 hours, 19 hours, or about 20 hours, or more.

In an embodiment, the entire assembly is about 7.4 meters, the height is about 1.6 meters and the width is about 2.2 meters. In an embodiment, the assembly weighs about 12,700 kg. Any other reasonable and commercially reasonable assembly dimensions are contemplated by this disclosure, thus a skilled person may modify these dimensions without exerting any more than routine work.

In an embodiment, the enclosure is completely covered to limit dust deposition. The assembly may be sterilized, for example, by injecting a mist of hydrogen peroxide into the enclosure. Covers may be dismantled in order to ensure a thorough cleaning, and the working parts will allow access to the inside of the device, in particular, to enable changing of the seals.

In an embodiment, the enclosure is made of a decontaminable material, particularly stainless steel. With an example high pressure of 4000 bar, the steel ideally possesses a high mechanical strength/integrity. In an embodiment, the material may be INCONEL 718.

In an embodiment, the internal diameter of the chamber may be 150 mm, and the outer diameter may be 440 mm. In this embodiment, an internal volume of 50 liters thus yields a free internal length of about 2.8 meters. At about 4000 bar, the compressibility of water is about 13%. Air pockets within samples may add to the overall compressibility calculations. In an embodiment, the free length at atmospheric pressure has been calculated with 20% compression, or about 3.4 meters. This gives a total chamber length of about 3.9 meters, and a mass of about 4900 kg.

In an embodiment, the assembly may prevent release of potentially contaminated water, by evacuating water contained in the chamber, then resealing end pieces. Inlets and outlets are provided by bores perpendicular to the axis of the enclosure. In a particular embodiment, the enclosure is a single piece.

In another embodiment, a sealing means for the piston/cylinder are provided on one side by the pressure piston seal (6), on the other side by a plug (7). Both sealing means may be stainless steel having a high mechanical strength. The sealing means may also be coated with, or consist of, any suitable material.

In an embodiment, the device moves laterally to enable loading and unloading of sample bags containing microorganisms, protein to be re-folded, and the like. The sample bags may be carried in containers that are sequentially driven into the device, like a small train. The chamber may be positioned on wheels running on rails, with the entire process being driven by a piston.

In an embodiment, the apparatus comprises a pressure booster, which may be made from stainless steel. However, since the pressure booster is not subjected to the same rigors as the piston/cylinder arrangement, the booster may be made of designed steel 1.4418. In an embodiment, the booster has the form of a cylinder of external diameter 620 mm and length 1750 mm, weighing 2200 kg. Inside is the piston. The inner diameter of the primary part is 540 mm. It contains up to 160 liters of oil. This volume is supplied by a hydraulic unit 310 bar with a flow rate of 250 liters/hour and installed outside the room. The pressure within the primary circuit is 310 bar.

The piston stroke may be about 940 mm. In the retracted position, it may be entirely released from the enclosure. However, the seal sealing in the housing is accessible to allow easy changing or cleaning, as the seal of the shutter, when the enclosure is fed in part loading/unloading.

The central part of the piston ram (5) may be hollow and may contain magnets to allow continuous and accurate movement and measurement of the piston's location. In the event of leakage of the seal, the pressure may be maintained by appropriately advancing the piston in order to compensate for the leak and ensure inactivation. The seal may be replaced during the next opening of the chamber.

In an embodiment, an actuator allows lateral movement of the multiplier to facilitate cleaning.

In another embodiment, a verification system laser may be provided to ensure proper alignment of the chamber and multiplier cylinders.

In another embodiment, the metal frame is designed to maintain the chamber and the multiplier in place when the latter exerts a pressure of 4000 bar within the enclosure. The frame may consist of several structural steel perforated plates. Weld finishing may be used to prevent liquid or mist form penetrating between the plates. The assembly may be coated with a protective paint or other suitable protective coating.

In an embodiment, the outside of the frame length is about 6.8 meters, its height is about 1.3 meters, and its weight is about 5600 kg.

In another embodiment, a pipe communicates hydraulic energy from a hydraulic unit. The pipe may be fixed and may be removed the multiplier is moved for maintenance.

In an embodiment, the enclosure is supplied with demineralized water via a pipe or suitable conduit. The pipe may be flexible and/or extendable so it need not be removed during the translation of the enclosure to the loaded/unloaded position. A second pipe or conduit may also be present, to allow the injection of compressed air for drying the chamber prior to opening. Part of the discharge pipe near the enclosure may also be flexible to accommodate the enclosure's working range of motion.

The evacuation of the enclosure is to the water treatment system of the building. Even in breach of pocket, as the bearing bar 4000 has been met, the water can be discharged without further treatment.

However, in case of failure to reach the bearing or holding time low, the water will be discharged to a tank independent, enabling an analysis to determine if contamination was a possible breach of pocket and specific treatment. It will be the same for the water used to rinse the enclosure.

Figure 1B:
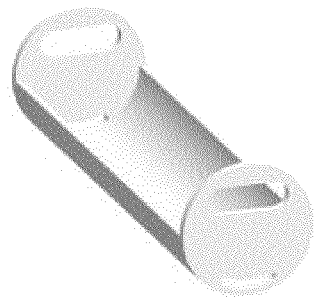
FIG. 1B depicts a representative sample pouch container.

In an embodiment of the first object, the hyperbaric device may be situated inside a housing having a general layout as schematized in FIG. 1A. The hyperbaric device may be designed to accommodate and receive sample holding devices, as illustrated in FIG. 1B. One of the important features of the device is that the microorganisms to be samples to be subjected to high pressure are contained within resilient pouches, instead of being "directly exposed" (for example, as a slurry of concentrated microorganisms) to the temperature changes and hydrostatic pressures. Instead, a slurry of concentrated microorganisms may be hermetically sealed within sample pouches, which are designed to fit into a pouch holder or receptacle, like that depicted in FIG. 1B. This approach to hyperbaric inactivation of microorganisms conveys multiple benefits, including consistency of sample processing, ease of equipment decontamination (in the event of pouch rupture), and reduced chance of batch contamination (e.g. even if one pouch becomes contaminated, the balance of the batch may remain clean).

In another embodiment of the first object, the device comprises a piston press device such as that depicted in FIG. 2A. The hyperbaric device (1) communicates controlled amounts of pressure to samples. Pressure is initially communicated to a primary fluid chamber (8) via a pressure intensifier chamber (9), which receives high pressure air/fluid from a pressure intensifier device. Pressure in the primary fluid chamber (8) is communicated to the high pressure fluid chamber (3) via the ram (5). Prior to the ram (5) extension, fluid enters a high pressure fluid chamber (3) via inlet (2) while pressure ram (5) is retracted. The ram (5) then extends into the position depicted in FIG. 2A, and seal (6) and plug (7) prevent the fluid from escaping from the high pressure fluid chamber (3). After completion of the pressurization and depressurization cycle (s), fluid is discharged via outlet (4). In an embodiment, the hyperbaric device comprises components as indicated in FIGS. 3, 4, 5 and 6.

Figure 7:
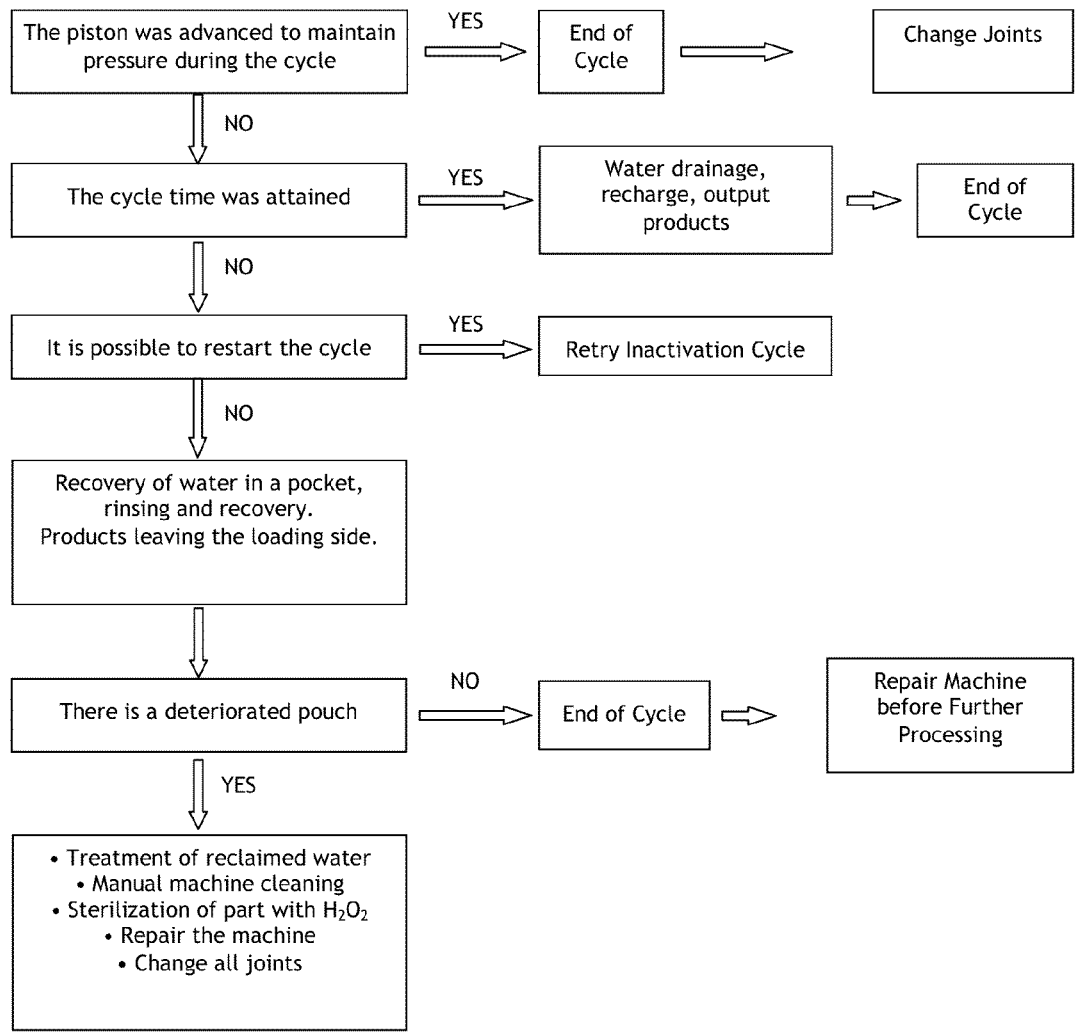
FIG. 7 is a flow diagram outlining safe operation of the hyperbaric device.
Figure 8:
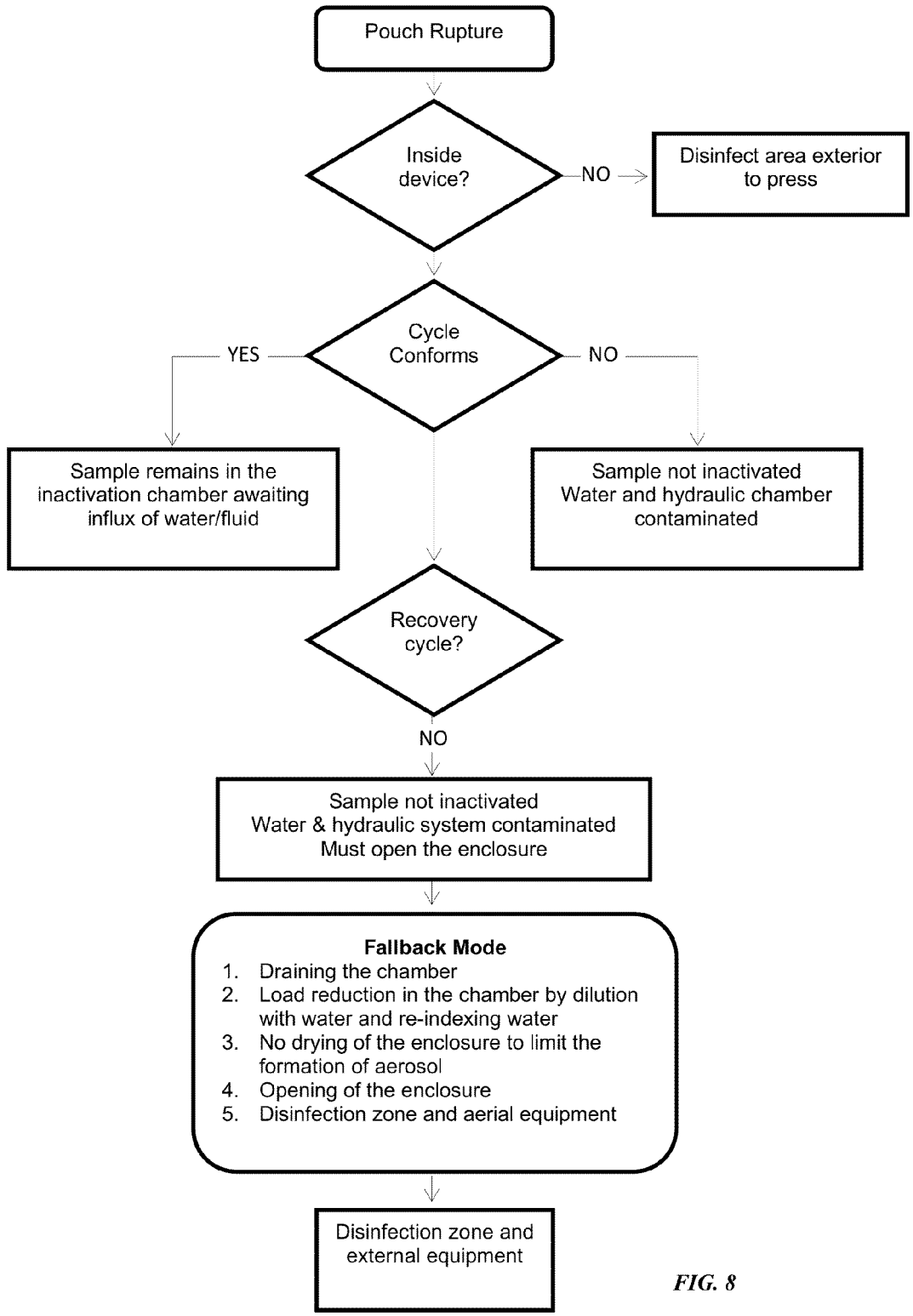
FIG. 8 is a flow diagram depicting actions to be taken in the case of a microorganism pouch failure/rupture within the high pressure device chamber.

In a particular embodiment, samples may be processed by the hyperbaric device according to the scheme outlined in FIG. 7. The disclosure thus provides a method for refolding/solubilization or disaggregating proteins, or for inactivating pathogens while retaining their immunogenicity, comprising the steps of:

1) placing a sample into a loading chamber;
2) extending a charging cylinder;
3) removing the sample from the loading chamber
4) retracting the charging cylinder;
5) positioning the sample into high pressure chamber;
6) extending a right cylinder advances to make a seal, enabling filling of a pressure multiplier with a fluid;
7) extending a left cylinder;
8) extending the left cylinder further to seal the high pressure chamber;
9) positioning a block which prevents the left cylinder from retracting on pressure application;
10) extending the right cylinder further to the left to increase pressure;
11) releasing the pressure;
12) withdrawing the block;
13) withdrawing the left cylinder to allow fluid draining;
14) returning the pressure multiplier to its starting position;
15) extending body to unload sample;
16) extending the charging cylinder.

In an embodiment, the device thus encompasses a means for receiving the pouch holders and delivering or positioning them to be exposed to the high hydrostatic pressure (HHP) produced by the action of the isostatic press/piston assembly. The device comprises means to subject the pouches to specific temperatures and pressures for specific periods of time. The device may have a local circulating water supply to precisely control the temperature of the device enclosure. The temperature of the enclosure and the circulating water supply may vary as indicated in Table 1. The device may apply a wide range of pressure, up to, for example 7000 bar, 8000 bar, 9000 bar, or 10000 bar. The device may comprise any number of components to achieve the required pressures and temperatures.

TABLE 1

Extremes and average temperatures within the 50 L
enclosure in response to changes in initial enclosure
temperature and process water temperature.

| T-water (° C.) | T-local (° C.) | T-min (° C.) | T-max (° C.) |
|---|---|---|---|
| 15 | 18 | 12.75 | 23.68 |
| 15 | 20 | 13.57 | 23.68 |
| 15 | 22 | 14.38 | 23.68 |
| 15 | 24 | 14.99 | 23.69 |
| 15 | 26 | 14.91 | 23.69 |
| 20 | 18 | 15.65 | 28.84 |
| 20 | 20 | 16.47 | 28.84 |
| 20 | 22 | 17.28 | 28.84 |
| 20 | 24 | 18.10 | 28.84 |
| 20 | 26 | 18.913 | 28.84 |
| 25 | 18 | 18.56 | 33.99 |
| 25 | 20 | 19.37 | 33.99 |
| 25 | 22 | 20.19 | 33.99 |
| 25 | 24 | 21.0 | 33.99 |
| 25 | 26 | 21.82 | 33.99 |
| 27 | 15 | 18.5 | 36 |
| 27 | 27 | 23.38 | 36.05 |

Pmax = 3500 bar; V = 1000 bar/min, Tea 1 h, 1 cycle process: Pmax = 3500 bar, V = 1000 bar/mn, plateau 1 hour, 1 cycle.

In another embodiment of the first object, the device further comprises a decontamination means. The decontamination means may provide general cleaning, as is required of any device used to produce pharmaceutical-grade biological product, and/or may be used to sterilize the device in the event of a sample pouch rupture.

In yet another embodiment, the device further comprises a sample inactivation status monitoring (SISM) means. The SISM means may comprise needles or other suitable probing devices adapted to aseptically remove defined portions of samples (from the sample pouches) at appropriate times throughout the hyperbaric inactivation process. Thus, the SISM means may assist the device user in determining when complete microorganism inactivation has been achieved. The SISM means may further include any number of automated viability assays useful for determining the inactivation status of the microorganisms. The device may be designed to automatically adjust conditions of temperature and time based upon data generated by the SISM means.

In embodiments where no SISM means is employed, inactivation kinetics are determined case by case, stored, and re-used as needed. During post-inactivation QC evaluation, samples may be determined to be inadequately inactivated, and may be subjected to additional round(s) of inactivation. QC data may be stored to adjust inactivation kinetics for a given type and concentration of microorganisms.

The device necessarily has at least one user programmable computer interface. The computer interface allows the device user to control all device functions. The interface control at least one data storage means, which records all data generated during the inactivation cycles, including, but not limited to, enclosure temperature, water temperature, and sample inactivation status. The interface may display the information in the form of graphs, outputted to a display means, and/or output the data to a user-convenient spread sheet or other suitable data processing software application.

A second object of the present disclosure is to provide methods for inactivating microorganisms while retaining their immunogenicity. In an embodiment, the method comprises the steps of subjecting the microorganisms to hyperbaric conditions under controlled temperatures for specified periods of time. The method may also comprise the steps of alternating between higher and lower pressures for specified periods of time and at specified temperatures. Extensive parameter modeling was performed, which is further described in the Detailed Description below. In general, the room temperature was from 15° C. to 26° C. and the device water temperature was from 15° C. to 27° C.

In another embodiment of the second object, the microorganisms are completely inactivated and incapable of causing infection, but are capable of eliciting an immune response in an animal susceptible thereto. In an embodiment, the immune response is a protective immune response. In another embodiment, the microorganisms are even more immunogenic than the same microorganisms that have been chemically inactivated. In yet another embodiment, the microorganisms are more immunogenic because the hyperbaric treatment has unmasked an immunogenic epitope.

A third object of the disclosure is to provide methods for determining the inactivation status of the microorganisms during and after performance of the hyperbaric inactivation methods. The inactivation status may be determined by any number of viability assays and may be used to adjust and optimize the hyperbaric inactivation parameters (i.e. pressure, temperature, time). Epitope integrity and/or availability may also be monitored and evaluated to determine the optimal inactivation parameters.

A fourth object of the disclosure is to provide immunogenic compositions comprising hyperbaric-inactivated microorganisms. In an embodiment, the immunogenic compositions are vaccine compositions, which elicit in vivo in an animal a protective immune response. The compositions may be safer and more effective than comparable compositions produced using chemically inactivated microorganisms. In an embodiment, the vaccines comprise hyperbarically-inactivated *leptospira* or *Erysipelothrix rhusiopathiae*.

As the disclosed hyperbaric device may be used to inactivate a wide variety of microorganisms, compositions comprising any microorganism so inactivated are envisioned by the instant disclosure.

A fifth object of the disclosure is to provide methods comprising using the hyperbaric device to refold/solubilize proteins for various molecular biological applications. In an embodiment, the present disclosure provides a method for producing a soluble, disaggregated, refolded or active protein expressed in prokaryotes or eukaryotes comprising the steps of (i) preparing inclusion bodies in a buffer containing no or low concentration of urea to form an inclusion body suspension; and (ii) subjecting the inclusion body suspension to a high pressure for a period of time.

In another embodiment, the present disclosure provides a method of producing a soluble, disaggregated, refolded or active protein expressed in prokaryotes or eukaryotes comprising the steps of (i) preparing the inclusion bodies in a buffer containing no or low concentration of urea to form inclusion body suspension; (ii) subjecting the inclusion body suspension to a gradual increase of pressure over a period of time; and (iii) maintaining the high pressure applied to the inclusion bodies for a period of time.

In one aspect, the buffer may contain Dithiothreitol (DTT). In another aspect, the DTT concentration may range from about 1 mM to about 100 mM, about 1 mM to about 90 mM, about 1 mM to about 70 mM, about 1 mM to about 60 mM, about 1 mM to about 50 mM, or about 1 mM, 2 mM, 3 mM, 4 mM, 5 mM, 6 mM, 7 mM, 8 mM, 9 mM, 10 mM, 20 mM, 30 mM, 40 mM, 50 mM. In one aspect, urea may not be present in the buffer. In another aspect, urea may be present in the buffer at the concentration of about 1M, about 2M, about 3M, about 4M, about 5M, about 6M, about 7M, about 8M, about 9 M, and about 10M.

In another aspect, the high pressure may be in the range from about 1000 bar to about 5000 bar, from about 2000 bar to about 4000 bar. The high pressure may be any pressure in the range from about 2000 bar to about 4000 bar, for example, but not limiting to, 2000 bar, 2100 bar, 2200 bar, 2300 bar, 2400 bar, 2500 bar, 2600 bar, 2700 bar, 2800 bar, 2900 bar, 3000 bar, 3100 bar, 3200 bar, 3300 bar, 3400 bar, 3500 bar, 3600 bar, 3700 bar, 3800 bar, 3900 bar, and 4000 bar.

In another aspect, the gradual increase of the pressure may be done continuously or stepwise. In one aspect, the gradual increase of the pressure is applied to the inclusion body suspension by continuously increasing the pressure at a constant rate over a period of time to reach the desired final high pressure. For example, the pressure is increased at the rate of about 200 bar/min-1000 bar/min continuously over about 2 min-10 min to reach 2000 bar, at the rate of about 200 bar/min-1000 bar/min continuously over about 3 min-15 min to reach 3000 bar, at the rate of about 200 bar/min-1000 bar/min continuously over about 4 min-20 min to reach 4000 bar, at the rate of about 200 bar/min-1000 bar/min continuously over about 5 min-25 min to reach 5000 bar. In another aspect, the gradual increase of the pressure is applied stepwise. For example, the pressure is increased at 1000 bar/min for one minute to reach 1000 bar, then the 1000 bar pressure is maintained for one hour to relax the protein, after the relaxation period, the pressure is increased again at 1000 bar/min for one minute to reach the final desired high pressure of 2000 bar.

To reach the final desired high pressure of 3000 bar, 4000 bar, and 5000 bar, the same stepwise increase of the pressure at 1000 bar/min for one minute with intermediate relaxation of protein for one hour may be employed. For example, the pressure is increased at 1000 bar/min for one minute to reach 1000 bar, then the 1000 bar pressure is maintained for one hour to relax the protein, the pressure is increased again at 1000 bar/min for one minute to reach the pressure of 2000 bar, then the 2000 bar pressure is maintained for one hour to relax the protein for the second time, the pressure is increased again at 1000 bar/min for one minute to reach the final desired pressure of 3000 bar. To reach the final desired pressure of 4000 bar, the pressure is increased at 1000 bar/min for one minute to reach 1000 bar, then the 1000 bar pressure is maintained for one hour to relax the protein, the pressure is increased again at 1000 bar/min for one minute to reach the pressure of 2000 bar, then the 2000 bar pressure is maintained for one hour to relax the protein for the second time, the pressure is increased again at 1000 bar/min for one minute to reach the final desired pressure of 3000 bar, then the 3000 bar pressure is maintained for one hour to relax the protein for the third time, the pressure is increased again at 1000 bar/min for one minute to reach the final desired pressure of 4000 bar.

The inclusion body suspension may be treated under the high pressure for about 10 hours to about 100 hours, about 20 hours to about 100 hours. The high pressure treatment is preferably for more than 24 hours, for example, for about 25 hours to about 100 hours, about 25 hours to about 80 hours, about 25 hours to about 60 hours, about 25 hours to about 50 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours.

In another embodiment, the present invention provides a method for producing a soluble, disaggregated, refolded or active protein expressed in prokaryotes or eukaryotes comprising the steps of (i) preparing the inclusion bodies in a buffer containing no or low concentration of urea to form inclusion body suspension; (ii) subjecting the inclusion body suspension to a gradual increase of pressure over a period of time; (iii) maintaining the high pressure applied to the inclusion bodies for a period of time; and (iv) recovering the protein by depressurization.

The protein may be selected from membrane proteins, surface antigens, or any protein of antigenic interest, including, but not limited to, *Leptospira* membrane proteins and *Bordetella* surface proteins.

Depressurization may be performed at the rate of about 83 bar/min-200 bar/min. The prokaryotes contemplated in the present invention may include *Avibacterium, Brucella, Escherichia coli, Haemophilus* (e.g. *Haemophilus suis*), *Salmonella* (e.g., *Salmonella enteritis, Salmonella typhimurium, Salmonella infantis*), *Shigella, Pasteurella*, and *Rimeirella*.

In prokaryotic systems, a number of expression vectors may be selected. Such vectors include, but are not limited to, the multifunctional *E. coli* cloning and expression vectors such as pBLUESCRIPT (Stratagene); piN vectors (Van Heeke & Schuster, J. Biol. Chem. 264:5503 5509 (1989)); and the like; PGEX Vectors (Promega, Madison, Wis.); In eukaryotic systems, the cell lines may be yeast (such as *Saccharomyces cerevisiae, Pichia pastoris*), baculovirus cells, mammalian cells, plant cells. The expression vectors of eukaryotic systems include, but are not limited to, pVR1020 or pVT1012 vectors (Vical Inc., San Diego, Calif.), PichiaPink Vector (Invitrogen, CA, USA), pFasBac TOPO vector (Invitrogen).

The method for producing a soluble, disaggregated, refolded or active protein expressed in prokaryotes or eukaryotes provided in the present invention may be used to solubilize any proteins. The proteins may include antibodies and insulin. The proteins may also include any therapeutic proteins, including clotting factors, peptide hormones, and the like.

In another embodiment, the present invention provides a composition or vaccine comprising a hyperbarically inactivated microorganism, including virus. The microorganism may, for example, be a protozoan (e.g. giardia, trypanosome, amoeba, falciparum, and the like), a virus (e.g. PCV2, Rota, West Nile, FMD, distemper, rabies, influenza, herpes, bovine diarrhea, infectious bursal disease, infectious rhinitis, adenovirus, poxvirus, and the like), or a bacterium (*Erysipelothrix rhusiopathiae, E. coli*, staphylococcus, coccidia, streptococcus, mycoplasma hyopneumoniae, helicobacter, and the like), and a pharmaceutically or veterinarily acceptable carrier, excipient, vehicle or adjuvant.

In another embodiment the present invention provides a method for hyperbarically inactivating a cell suspension of *Bordetella pertussis* (*B. pertussis*) comprising the steps of:
 (a) producing a cell suspension of *Bordetella pertussis* in a culture medium,
 (b) concentrating the cell suspension produced in said culture medium, optionally supplemented with saline (0.9% NaCl) or a buffer solution that does not exceed 25% of the final volume (V/V),
 (c) heating the concentrated cell suspension at a temperature comprised between 50° C. to 54° C., and
 (d) inactivating the heat-treated concentrated cell suspension by high pressure treatment wherein the high pressure is higher than 2000 bars but lower than 6000 bars.

Any liquid medium convenient for the culture of *B. pertussis* can be used. It can be, in particular, the Cohen Wheeler medium (American Journal of Public health, 1946, 36, 371-376), the Verwey medium (J. Bacteriol. 1949; 58:127-134) or a chemically defined medium as described by Stainer D. W. et al. (Journal of General Microbiology 1971, 63, 211-220). Preferably the liquid medium is the Cohen Wheeler medium which derives from the original fluid medium of Hornibrooks and has been shown to be especially suitable for large scale cultivation of B. pertussis. The composition of the Cohen Wheeler medium comprises a nitrogen source like Casamino acids or casein hydrolyzate, a mixture of inorganic salts (monopotassium phosphate, magnesium chloride, calcium chloride, ferrous sulfate, copper sulfate), soluble starch, a yeast extract, and a cysteine derivative selected from the group consisting of cysteine, a salt of cysteine like cysteine hydrochloride, cystine and glutathione hydrochloride. Optionally the composition of the Cohen wheeler may contain some additional components such as amino acids and/or sodium chloride. Usually the yeast extract is under the form of a hydrolyzed yeast extract or an autolyzed yeast extract and has been dialyzed or ultra-filtered.

The suspension of B. pertussis produced is harvested and concentrated, for instance by centrifugation and resuspension of the cell pellet with a reduced volume of the culture supernatant that is optionally supplemented with saline (0.9% NaCl) or a buffer solution such as a phosphate buffer solution, that does not exceed 25% of the final volume (V/V) or by tangential flow filtration, such that the final cell concentration is usually between $10^9$ and $10^{13}$ CFU/ml. Usually, the final volume of the concentrated cell suspension is 10 to 20 fold less than the volume of the harvest. The concentrated suspension of B. pertussis is then heated at a controlled temperature comprised between 50° and 54° C. (limits inclusive) for a period of time which reduces the cell viability of a factor of about $10^4$ to $10^6$ (measured in CFU/ml), and the toxicity of the pertussis toxins while preventing the thermal denaturation of the proteins. This effect can be achieved by heating the concentrated suspension for 30 minutes at a controlled temperature between 50° and 54° C. (limits inclusive). Preferably, the time period wherein the temperature is between 38° C. and 54° C. is also taken into account in the heating of the concentrated suspension. For instance, the time period wherein the concentrated suspension is heated between 38° C. and 54° C. which includes the 30 minute period where the temperature is between 50 and 54° C. can last between 40 and 90 minutes, or between 50 and 80 minutes or even between 55 and 70 minutes (limits inclusive). The setting of these temperature parameters can be easily monitored by an automatic controlled heating program according to which the temperature of the concentrated cell suspension is stepwise increased from 38° C. to 50° during a defined time period (for instance 10 to 20 minutes), followed by a 30 minute time period wherein the temperature is maintained between 50 and 54° C. (limits inclusive) and finally a defined time period (for instance 10 to 20 minutes) where the temperature of the concentrated cell suspension is stepwise decreased from 50° C. to 38° C.

The heat-treated and concentrated cell suspension of B. pertussis is finally fully inactivated by hyperbaric treatment in conditions that preserve the immunogenicity of the whole inactivated bacteria. This effect is achieved by subjecting the heat-treated and concentrated cell suspension to a high pressure which is higher than 2000 bar but lower than 6000 bar using in particular the hyperbaric device of the present invention. It can be for instance but not limiting to 2500 bar, 3000 bar, 3500 bar, 4000 bar, 4500 bar, 5000 bar, 5500 bar. The higher the pressure, the shorter the high pressure treatment is required. More particularly, the high pressure may be any pressure in the range from 3000 bar to 5000 bar (limits included), for example but not limiting to 3000 bar, 3100 bar, 3200 bar, 3300 bar, 3400 bar, 3500 bar, 3600 bar, 3700 bar, 3800 bar, 3900 bar, 4000 bar, 4100 bar, 4200 bar, 4300 bar, 4400 bar, 4500 bar, 4600 bar, 4700 bar, 4800 bar, 4900 bar, 5000 bar. In this range of high pressure, the high pressure treatment is at least 15 minutes long but usually the duration is within the range from 15 minutes to 180 minutes and adjusted according to the strength of the high pressure which is applied to the heat-treated and concentrated cell suspension. When the high pressure to be applied is 3000 bar, the high pressure treatment shall last more than 30 minutes, for instance 90 minutes, 100 minutes, 110 minutes, 120 minutes, 130 minutes, 140 minutes, 150 minutes, 160 minutes, 170 minutes, or 180 minutes. On the other hand, when the high pressure to be applied is in the range from 4000 bar to 5000 bar (limits included) the duration of the high pressure treatment can be shortened, for instance 30 minutes or even less but by precaution it is advised to treat during a time period from 30 minutes to 180 minutes. It can be for instance but not limiting 30 minutes, 40 minutes, 50 minutes, 60 minutes, 70 minute, 80 minutes, 90 minutes, 100 minutes, 110 minutes, 120 minutes, 130 minutes, 140 minutes, 150 minutes, 160 minutes, 170 minutes, or 180 minutes, for instance a treatment for 90 minutes at 4000 bar. In this range of high pressure and time period, it has been observed a lack of recovery phenomenon which means that the inactivation of the bacteria is irreversible and definitive since there are no more viable bacteria after a resting period.

The fully inactivated concentrated suspension of B. pertussis obtained by the combination of heat treatment and hyperbaric treatment according to the process of the invention retains good immunogenic properties since its potency is well conserved and comparable to the potency of a reference vaccine calibrated against the international standard for Pertussis vaccine or an equivalent standard vaccine approved by the international regulatory authority. The toxins in the preparation are well neutralized since the mouse weight gain test gives satisfactory results. The observation by scanning electron microscopy reveals that there are no visible morphological changes in the population of inactivated bacteria after heat and hyperbaric treatments. It is essentially made of whole inactivated bacteria without significant proportion of lytic bacteria and looks like the population of bacteria that have been inactivated by a chemical treatment with merthiolate. Furthermore, the process of the invention can easily be carried out at an industrial scale since the hyperbaric device of the invention has been designed to treat important volumes of biological material (50 liters or more). The process of the invention represents a good alternative to the classical chemical inactivation of B. pertussis by merthiolate and represents a new opportunity for manufacturing an inactivated whole cell Pertussis vaccine. Accordingly, a further object of the present invention is relating to a process for manufacturing a whole cell Pertussis vaccine comprising the steps of 1) inactivating a concentrated cell suspension of Bordetella pertussis by heat and hyperbaric treatments as described in the invention and 2) diluting the inactivated concentrated cell suspension of B. pertussis in a pharmaceutically acceptable excipient before being divided up into packaging devices.

The pharmaceutically or veterinarily acceptable carriers or adjuvant or vehicles or excipients are well known to the one skilled in the art. The pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

The subunit (protein) vaccine may be combined with adjuvants, like oil-in-water, water-in-oil-in-water emulsions based on mineral oil and/or vegetable oil and non-ionic surfactants such as block copolymers, TWEEN®, SPAN®. Such emulsions are notably those described in page 147 of "Vaccine Design—The Subunit and Adjuvant Approach", Pharmaceutical Biotechnology, 1995, or TS emulsions, notably the TS6 emulsion, and LF emulsions, notably LF2 emulsion (for both TS and LF emulsions, see WO 04/024027). Other suitable adjuvants are for example vitamin E, saponins, and Carbopol® (Noveon; see WO 99/51269; WO 99/44633), aluminum hydroxide or aluminum phosphate ("Vaccine Design, The subunit and adjuvant approach," Pharmaceutical Biotechnology, vol. 6, 1995), biological adjuvants (i.e. C4b, notably murine C4b (Ogata R T et al.) or equine C4b, GM-CSF, notably equine GM-CSF (U.S. Pat. No. 6,645,740)), toxins (i.e. cholera toxins CTA or CTB, *Escherichia coli* heat-labile toxins LTA or LTB (Olsen C W et al.; Fingerut E et al.; Zurbriggen R et al. Peppoloni S et al.), and CpG (i.e. CpG #2395 (see Jurk M et al.), CpG #2142 (see SEQ. ID. NO: 890 in EP 1,221,955)). Other adjuvants include polyA-polyU, dimethyldioctadecylammonium bromide (DDA) ("Vaccine Design The Subunit and Adjuvant Approach", edited by Powell and Newman, Pharm. Biotech., 6: p. 03, p. 157); N,N-dioctadecyl-N',N'-bis(2-hydroxyethyl) propanediamine (such as AVRIDINE®) (Ibid, p. 148); and carbomer, chitosan (see U.S. Pat. No. 5,980,912 for example); polymers of acrylic or methacrylic acid, maleic anhydride and alkenyl derivative polymers, cationic lipids containing a quaternary ammonium salt, cytokines. Any combination of adjuvants may also be used.

In one embodiment, a solution of adjuvant, especially of carbomer (Pharmeuropa, vol. 8, No. 2, June 1996), is prepared in distilled water, advantageously in the presence of sodium chloride, the solution obtained being at an acidic pH. This stock solution is diluted by adding it to the desired quantity (for obtaining the desired final concentration), or a substantial part thereof, of water charged with NaCl, advantageously physiological saline (NaCl 9 g/l) all at once in several portions with concomitant or subsequent neutralization (pH 7.3 to 7.4), advantageously with NaOH. This solution at physiological pH is used for mixing with the vaccine, which may be especially stored in freeze-dried, liquid or frozen form. The polymer concentration in the final vaccine composition can be from 0.01% to 2% w/v, from 0.06 to 1% w/v, or from 0.1 to 0.6% w/v.

Another aspect of the invention relates to a method for inducing an immunological response in an animal against one or more antigens or a protective response in an animal against one or more pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more *Leishmania* pathogens in a prime-boost administration regime, which is comprised of at least one primary administration and at least one booster administration using at least one common polypeptide, antigen, epitope or immunogen. The immunological composition or vaccine used in primary administration may be same, may be different in nature from those used as a booster. The prime-administration may comprise one or more administrations. Similarly, the boost administration may comprise one or more administrations. The prime-boost administrations may be carried out 2 to 6 weeks apart, for example, about 3 weeks apart. According to one embodiment, a semi-annual booster or an annual booster, advantageously using the subunit (protein) vaccine, is also envisioned.

A variety of administration routes may be used in addition to subcutaneously or intramuscularly, such as intradermally or transdermally.

The composition or vaccine according to the invention comprise or consist essentially of or consist of an effective quantity to elicit a therapeutic response of one or more polypeptides as discussed herein; and, an effective quantity can be determined from this disclosure, including the documents incorporated herein, and the knowledge in the art, without undue experimentation.

For the composition or vaccine comprising the expressed protein of the present invention, a dose may include, from about 1 µg to about 2000 µg, about 5 µg to about 1000 µg, about 10 µg to about 100 µg, about 20 µg to about 1000 µg, about 30 µg to about 500 µg, or about 50 µg to about 500 µg. The dose volumes can be between about 0.1 ml to about 10 ml, or between about 0.2 ml to about 5 ml.

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of T. parva are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

Compositions

The present invention relates to a hyperbaric-inactivated microorganism vaccine or composition which may comprise hyperbaric-inactivated microorganisms and a pharmaceutically or veterinarily acceptable carrier, excipient, or vehicle, which elicits, induces or stimulates a response in an animal.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles.

Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of Use and Article of Manufacture

The present invention includes the following method embodiments. In an embodiment, a method of vaccinating an animal comprising administering a composition comprising a hyperbarically-inactivated microorganism and a pharmaceutical or veterinarily acceptable carrier, excipient, or vehicle to an animal is disclosed. In one aspect of this embodiment, the animal is a porcine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of pig or swine compositions, based on bacterial antigens, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as porcine, with a virulent strain of *Erysipelothrix rhusiopathiae*. Both homologous and heterologous strains are used for challenge to test the efficacy of the vaccine. The animal may be challenged by IM or SC injection, spray, intra-nasally, intra-ocularly, intra-tracheally, and/or orally. Samples from joints, lungs, brain, and/or mouth may be collected before and post-challenge and may be analyzed for the presence of *Erysipelothrix rhusiopathiae*-specific antibody.

The compositions comprising the inactivated microorganisms of the invention used in the prime-boost protocols are contained in a pharmaceutically or veterinary acceptable vehicle, diluent or excipient. The protocols of the invention protect the animal from virulent forms of the microorganisms and/or prevent disease progression in an infected animal.

The various administrations are preferably carried out 1 to 6 weeks apart. Preferred time interval is 3 to 5 weeks, and optimally 4 weeks according to one embodiment, an annual booster is also envisioned. The animals, for example pigs, may be at least 3-4 weeks of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

Another embodiment of the invention is a kit for performing a method of eliciting or inducing an immunological or protective response against a microorganism in an animal comprising a hyperbarically inactivated immunological composition or vaccine and instructions for performing the method of delivery in an effective amount for eliciting an immune response in the animal.

Another embodiment of the invention is a kit for performing a method of inducing an immunological or protective response against virulent microorganisms in an animal comprising a composition or vaccine comprising a hyperbarically-inactivated microorganism of the invention, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980,912). In an embodiment, the adjuvant may be inactivated bacteria, an inactivated virus, fractions of inactivated bacteria, bacterial lipopolysaccharides, bacterial toxins, or derivatives or combinations.

In an embodiment, the adjuvant comprises whole bacteria and/or viruses, including *H. parasuis, clostridium*, swine immunodeficiency virus (SIV), porcine circovirus (PCV), porcine reproductive and respiratory syndrome virus (PRRSV), *Mannheimia, Pasteurella, Histophious, Salmonella, Escherichia coli*, or combinations and/or variations thereof. In several embodiments, the adjuvant increases the animal's production of IgM, IgG, IgA, and/or combinations thereof.

The invention will now be further described by way of the following non-limiting examples.

EXAMPLE 1

Device Parameter Development

The instant disclosure provides, in part, a high pressure device, which 1) completely inactivates microorganisms (rendering them non-infectious); and 2) retains and/or improves the immunogenic potential (immunogenicity) of the microorganisms. Previous devices, designed to reduce microorganism burden in food (e.g. juices) or biologics (e.g. blood products or recombinant Factor VIII), lacked these features, which are critical to producing safe, effective, hyperbarically-inactivated vaccine components. During the establishment of microorganism inactivation kinetics, boundary conditions were evaluated, including extremes in temperature and pressure, and extremes in pressure gradients. Antigenicity and immunogenicity of the hyperbarically inactivated microorganisms were also evaluated to help define device requirements, as were device heating/cooling mechanisms. The homogeneity of the device's operating temperature was also modeled, to develop optimal hyperbaric inactivation conditions. Determining the extremes of temperatures in the device by modelization allowed inactivation parameter (pressure, time and temperature) validation.

Parameter modeling. A finite element method using the calculation code Cats3M was developed and used to evaluate the heat exchange in a in a high pressure (several hundred MPa) chamber for the inactivation of viruses and/or bacteria. The calculation was performed on several 2D axisymmetric enclosure geometries to better understand the effect of the mechanical configuration of the enclosure on the thermal response of the latter. The purpose of the study was to design a large enclosure volume (about 100 L), with the goal of limiting the heterogeneity in temperature, and to meet the constraints of the biological inactivation mechanism. The high pressure process was developed and studied over several cycles of compression-decompression with a relaxation time under high pressure and at zero pressure.

The developed algorithm allowed visualization of the isotherms throughout the process. The average temperature and heterogeneity in temperature versus time were extracted from these calculations. The validity of the algorithm was verified by comparison with several experimental studies. We have tested different fluids to transmit pressure, and have evaluated the impact of factors such as the speed of compression and decompression, the initial temperature of the pressure-transmitting fluid, and the maximum pressure reached.

The results indicate a good fit with the experimental measurements and allow profiling an experimental protocol and setting the geometry of the enclosure using the algorithm to guide its design (a comparison between experimental and modeled temperature profiles on an isostatic press, ¼ liter volume piston mode). Both measures converge towards a value of about 0.16% to Cp (4236 Jg-1·K-1 and 4243 Jg-1·K-1) at a temperature of 13° C. This gives us at this temperature a thermal capacity of 4240±0.004 Jg-1·K-1. The specific heat of water at 20° C. is 4.1813 Jg-1·K-1 [4], which is a difference of 1.4%, with measurements made on the biological product to be processed by pressing method. Given the small differences in physical properties between the biological fluid and water, these results were quite consistent and also confirmed the applicability of the model to hyperbaric inactivation of microorganisms. Thus, modeling of cycles performed for the water by varying the rate of compression and decompression, the initial temperature of the pressure transmitting fluid, and the maximum pressure is reached, wee representative of the actual case of treating a biological fluid.

Now that inventors have provided the instant disclosure, the skilled person will be able to successfully inactivate any number of microorganisms through routine optimization of the parameters discussed herein.

EXAMPLE 2

Efficacy in Porcine of Hyperbaric-Inactivated *Erysipelothrix rhusiopathiae*

*Erysipelothrix rhusiopathiae* was inactivated using the device of the instant disclosure. It was surprisingly found, during efforts to hyperbarically inactivate *E. rhusiopathiae*, that there existed a "recovery phenomenon," whereby the bacteria exhibited the ability to repair their enzyme systems after several days of storage at room temperature. Therefore, the hyperbaric device pressure, temperature, and time parameters had to be adjusting to compensate for this phenomenon. Several inactivating conditions were investigated, including 4000 bar for 90 minutes at 37° C.

Figure 18:
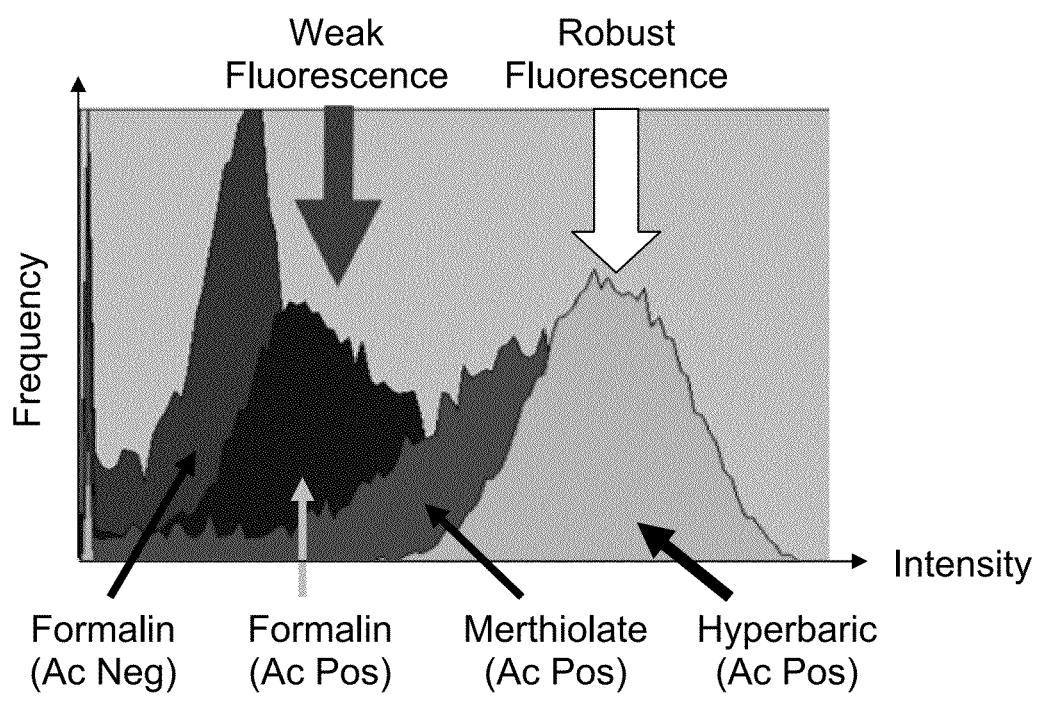

One hundred liters of *Erysipelothrix rhusiopathiae* bacterial culture was inactivated by three different methods to produce Active Principles (PA): 1) chimerical; 2) sodium formaldehyde; and 3) hyperbaric (4000 bar, 90 minutes, 37° C.). Samples from each of the inactivated fractions were characterized, and SpaA protein (Surface Protein Antigen A), a protein known to be protective antigen of *E. rhusiopathiae*, was detected in all three fractions, including the hyperbaric inactivated fraction (monoclonal Abs, Western blotting, data not shown). Sera from mice immunized with PA contain three polyclonal antibodies against this protein. Further, sera from pigs vaccinated with a recombinant protein SpaA have antibodies that recognize the protein SpaA in merthiolate- and hyperbaric-inactivated PA. Finally, the three PA were stained by a fluorescent monoclonal SpaA antibody, and distributions of marked/unmarked bacterial populations varied markedly depending upon the mode of inactivation: 95% of hyperbaric inactivated bacteria were marked, with a mean fluorescence intensity of 24 arbitrary units, while only 79% of merthiolate inactivated bacteria were marked, with a mean intensity of only 7 units (FIG. 18). This result suggests chemical inactivation damaged the antigenic proteins present in bacteria.

Figures 19, 20:
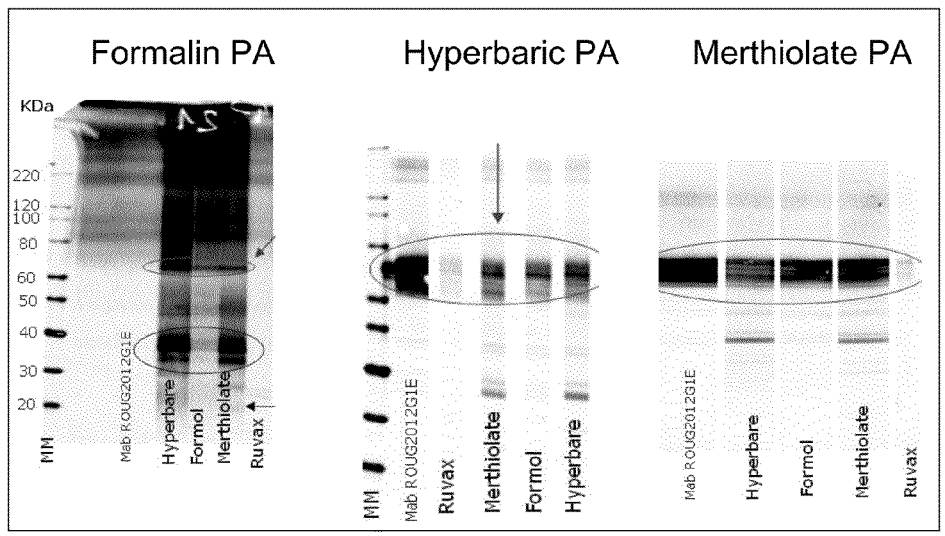

Vaccination trial on laboratory animals. Mice were vaccinated with each of the three inactivated *Erysipelothrix rhusiopathiae* (merthiolate, formaldehyde, and hyperbaric), then challenged with live/virulent *E. rhusiopathiae* by IP injection. One hundred percent of mice vaccinated with hyperbaric inactivated survived the challenge (FIG. 20).

Figure 23:
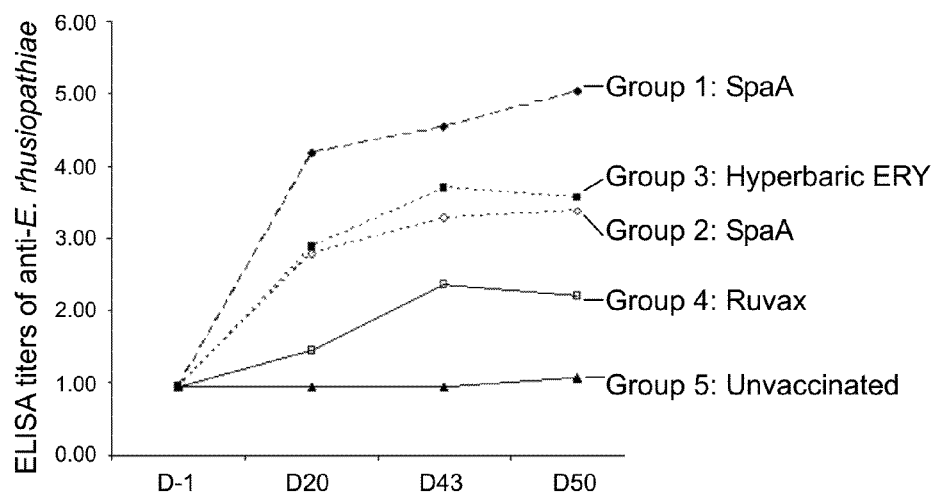
Figure 24:
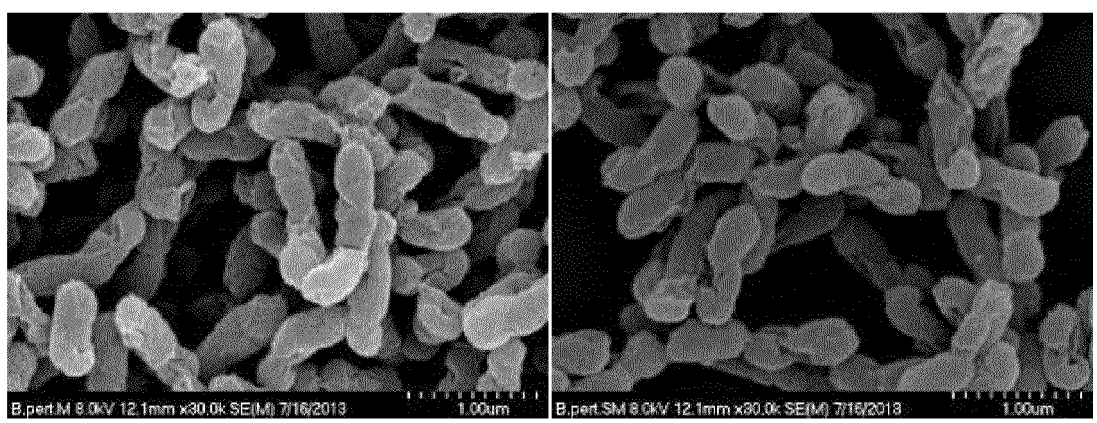

Vaccination of Target Animal: Pigs. Groups of 7 pigs were vaccinated with either chemical- or hyperbaric-inactivated bacteria, or a recombinant SpaA protein, then challenged with live bacteria injected intradermally (serological data provided in FIG. 23). The appearance of skin lesions was monitored, and the vaccine was considered effective if it fully protected against lesion formation. All vaccinated animals were completely protected against two *E. rhusiopathiae* strains (serotypes 1 and 2).

T Cell Response Induced by Hyperbaric Inactivated *E. rhusiopathiae*. Increasing dilutions of the three *E. rhusiopathiae* placed in the presence of peripheral blood mononuclear cells (Pumps) of pig vaccinated with the recombinant protein and the T-cell response SpaA specific bacterial antigens quantified using an ELI Spot assay revealed IFN. This study showed better ex vitro reactivation response of T cells specific for the hyperbaric-inactivated antigen in all dilutions tested. In addition, 42 days after vaccination, when the frequency of specific T cells decline, this effect was even more pronounced, clearly suggesting a better quality of antigen (for the hyperbaric inactivated fraction).

Mapping T-Cell Epitopes. A bank of overlapping peptides of the protein LOG was used to determine which T-cell epitope were activated by the various inactivated bacteria (principle active, PA). This study showed that some epitopes were much better recognized by the animals vaccinated with hyperbaric inactivated PA than those vaccinated with a chemically inactivated PA.

Finally, Sera from pigs vaccinated with different vaccine preparations were assayed for levels of specific antibodies to *Erysipelothrix rhusiopathiae*. IgG1 and IgG2 were induced, and among the 3 inactivation methods, the titers of IgG1 and IgG2 were higher for the animals vaccinated with the hyperbaric-inactivated bacterium as compared to animals vaccinated with the chemically bacteria.

EXAMPLE 3

Hyperbaric Inactivation of *Leptospira*

Three vaccine strains of leptospires were evaluated for hyperbaric inactivation: *Leptospira canicola*, *Leptospira grippotyphosa* and *Leptospira Icterohaemorrhagiae*. Preliminary tests showed that *leptospira* bacteria were successfully inactivated at a pressure of 2500 bar for three tested inactivation temperatures (10° C., 20° C. and 30° C.). These results confirm those obtained by Carla Silva in 2000 (C. Silva et al, 2001). Numerous publications have focused on the research and identification of protective antigens in different strains of leptospires (P. Cullen et al, Infection And Immunity, 2005): lipopolysaccharides or LPS, a major component of the surface of the bacteria responsible for antigen and agglutination tests; a transmembrane protein OmpL1; and lipoprotein anchored in the membrane by their N-terminus and providing partial protection in laboratory animals: LipL32, LipL36 and LipL41

Figure 9:
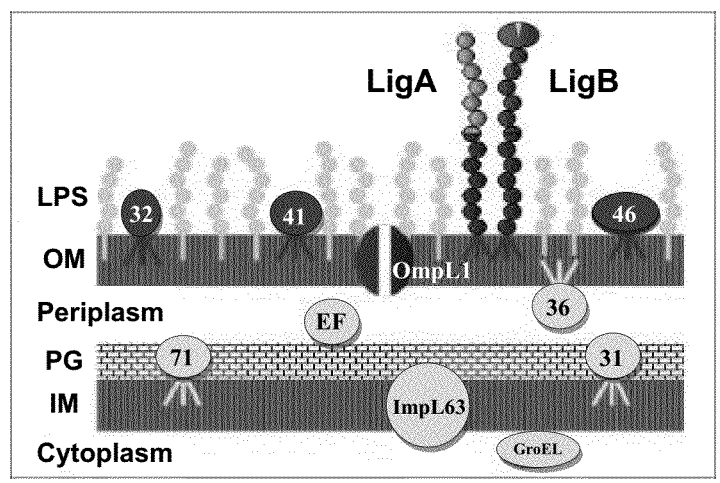
FIG. 9 is a schematic representation of the *Leptospira* presumed protective antigens.

Recently, surface proteins (LigB and LigA) with repeats of 90 amino acids resembling immunoglobulin conferred partial protection of laboratory animals for testing counterparts (W. Yan et al, Microbes and Infections, 2009). FIG. 9 provides a schematic representation of the presumed protective antigens in *Leptospira*. To characterize the antigenicity of different bacterial suspensions after hyperbaric inactivation, the study of LPS, lipoprotein (LipL32/41/46) anchored in the outer membrane, and virulence factors (LigA/B) was performed on cultures of three Lepto serovars. The treatment conditions included non-inactivated, chemically-inactivated by sodium merthiolate (0.1 g/l, 24° C. to 29° C.), and hyperbaric inactivation at 20° C. according to Table 2.

TABLE 2

Description of the different suspensions of *Leptospira* and inactivation conditions.

|  | L. icterohaemorrhagiae | L. canicola | L. grippotyphosa |
|---|---|---|---|
| ID | Li84 | Lc87 | ATCC 23604 |
| O.D. 450 nm | 0.709 | 0.53 | 0.73 |
| FTU | 341 | 256 | 400 |
| FACS | 1.8*10E9 U/ml | 1.2*10E9 U/ml | 2.4*10E9 U/ml |
| INACTIVATION Hyperbaric | 2500b/60' (inac1) | 2500b/60' (inac1) | 2500b/60' (inac1)- 2500b/30' (inac2) |
| Inactivation Control | — | — | — |
| INACTIVATION Chemical | Merthiolate 0.1 g/L | | |
| Inactivation Control | — | — | — |

FTU: Turbidity Units. FACS: Fluorescence Activated Cell Sorting.

All conditions tested inactivation led to the inactivation of leptospires. Inactivation controls are those routinely used and their detection threshold is known and sufficiently sensitive to detect a bacterium living in a few milliliters. Briefly, the samples are centrifuged the product control to collect inactivated bacteria in the pellet and remove as much inactivating agent in the supernatant and then deliver the pellet culture in fresh medium. The same medium is validated by a viability test and identifies growth by seeding as few as 10 *Leptospira* bacteria. Following inactivation, antigenicity studies were conducted using three types of sera: 1) Monoclonal anti-LPS, not intersecting between different serovars; 2) monospecific polyclonal antibodies lipoprotein (LIPL); and 3) polyclonal antibodies specific for non LigA/B (recognizing common epitopes). Table 3 details the nature of the different antibodies.

TABLE 3

Antibodies used for *Lepto* antigenicity studies.

| M(Monoclonal)/ P (Polyclonal) | LPS | LipL32 | LipL41 | LipL46 | LigA | LigB |
|---|---|---|---|---|---|---|
| LI | M | P | P | P |  | P |
| LC | M | P | P | P |  | P |
| LG | M | P | P | P |  | P |

M: Monoclonal Ab; P: Polyclonal Ab.

Figure 10:
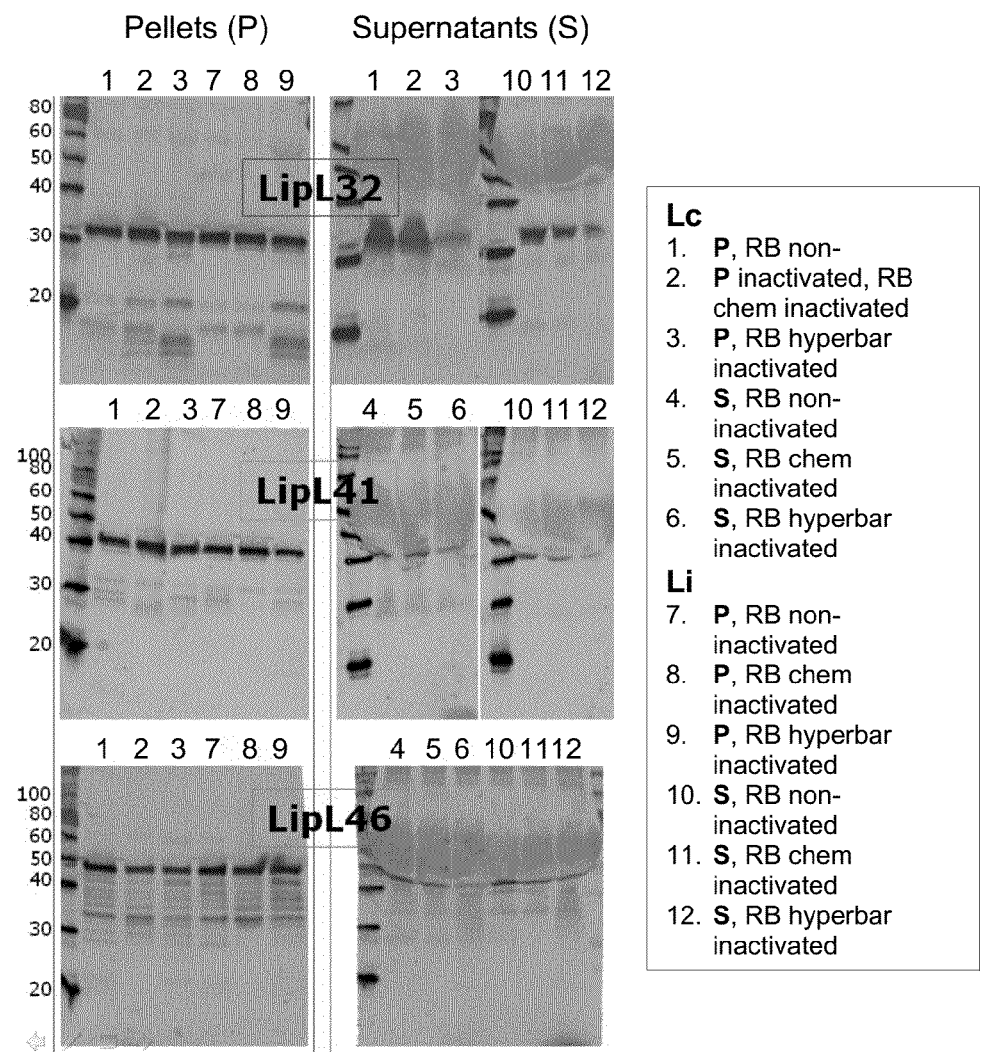
FIG. 10 depicts Western Blot results for *leptospira* suspensions previously subjected to either chemical, hyperbaric, or no inactivation. Strains: *L. canicola, L. ictero
Figure 11:
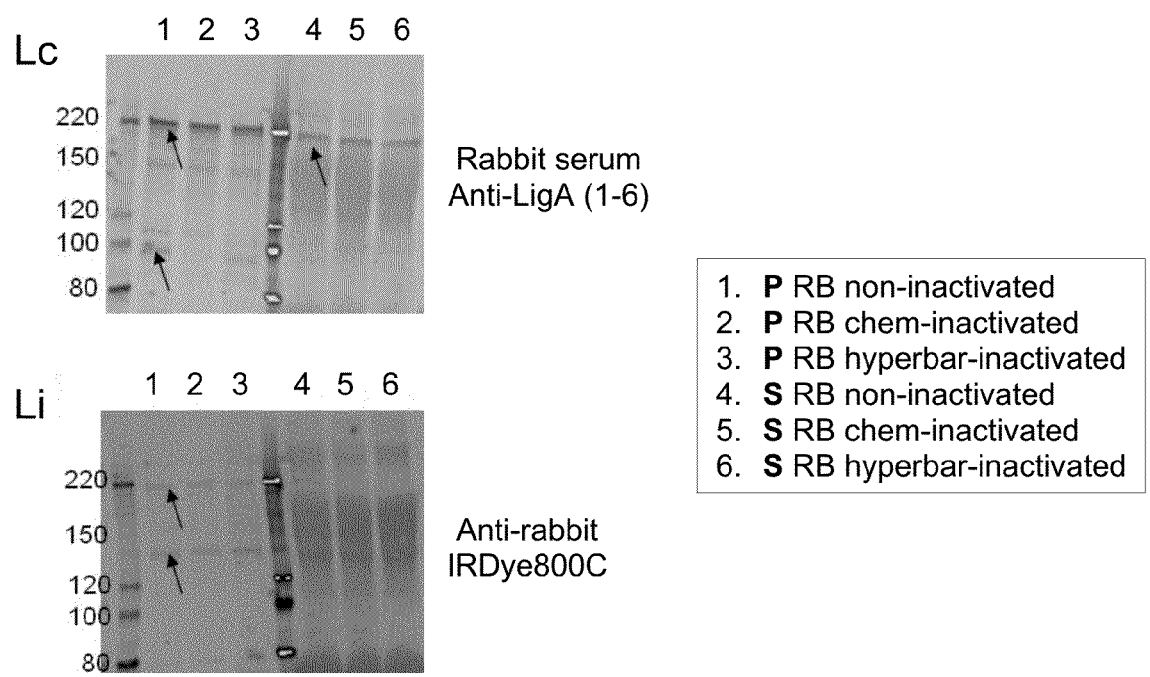
Figure 12:
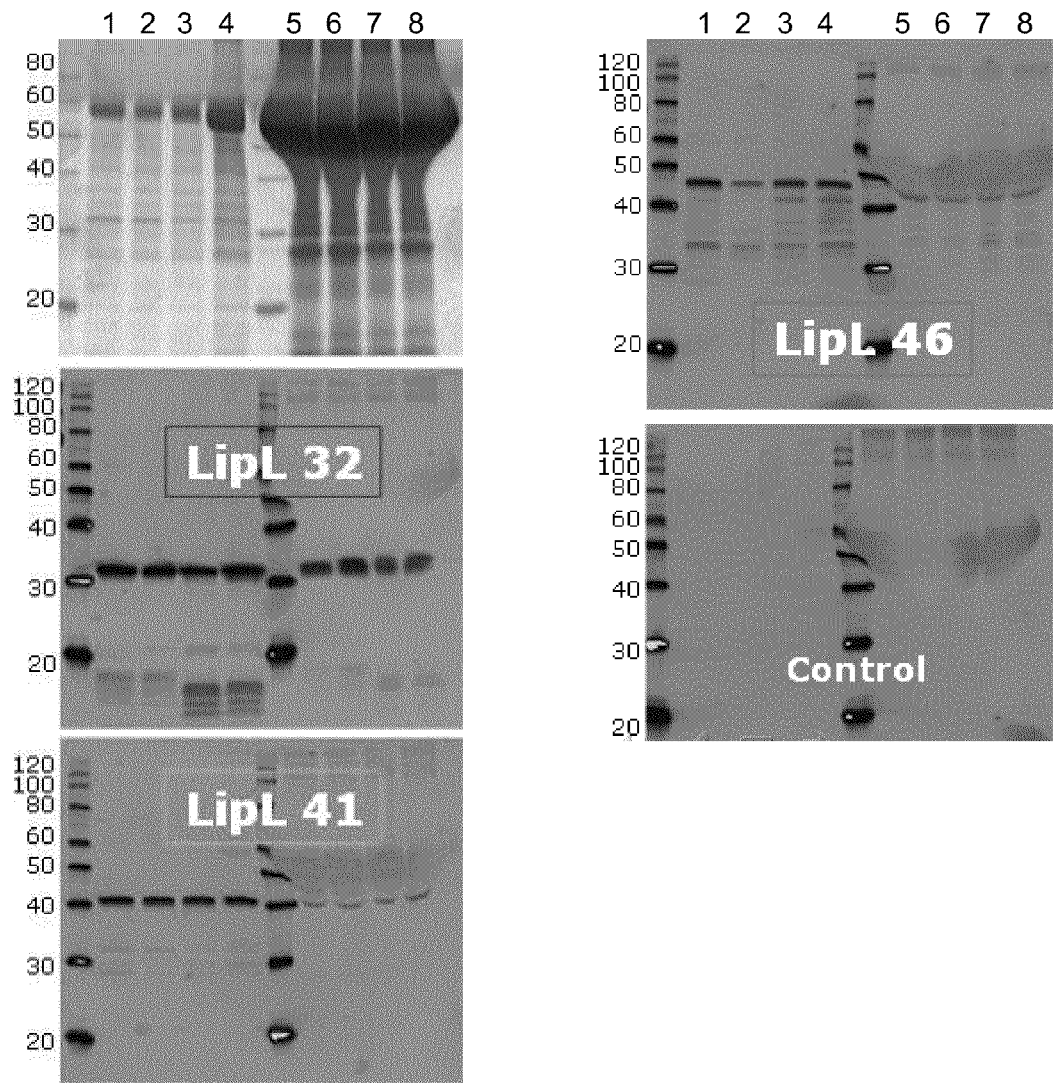
Figure 13:
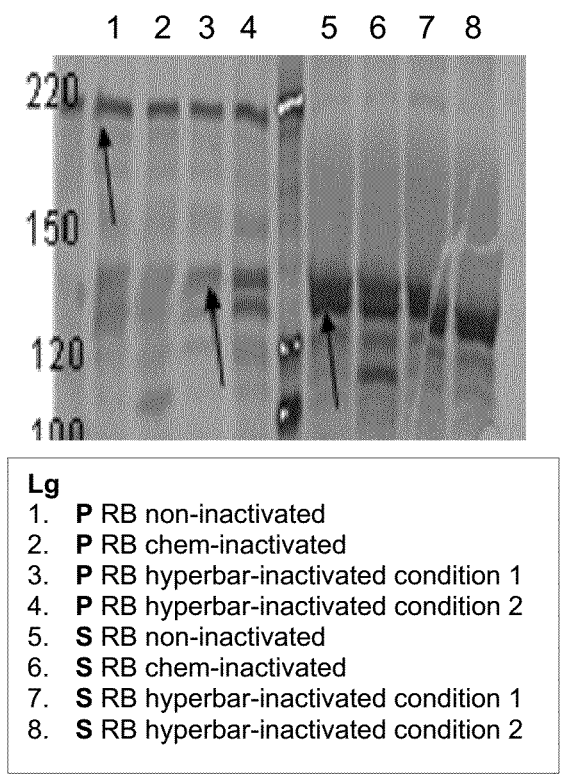

A publication mentioning the disappearance of certain membrane proteins after hyperbaric treatment (M. Ritz et al, International Journal Of Food Microbiology, 2000)—these antigens will be sought in the whole bacterial suspensions (or Brutes Crops-RB), pellets or the supernatants of these bacterial suspensions after centrifugation, before and after inactivation. Western blots of these antigens for the three strains are presented in FIGS. 10-13. Antigens LipL32, LipL41 and LipL46 (FIGS. 10 and 12), were recognized by the polyclonal antibodies for all three treatments. Hyperbaric inactivation did not alter antigenicity; however, some degradation of LipL32 and LipL46 antigen was noticed after hyperbaric treatment, when compared to the non-inactivated or chemically inactivated groups (especially for *L. grippotyphosa*, FIG. 12).

Figure 14A:
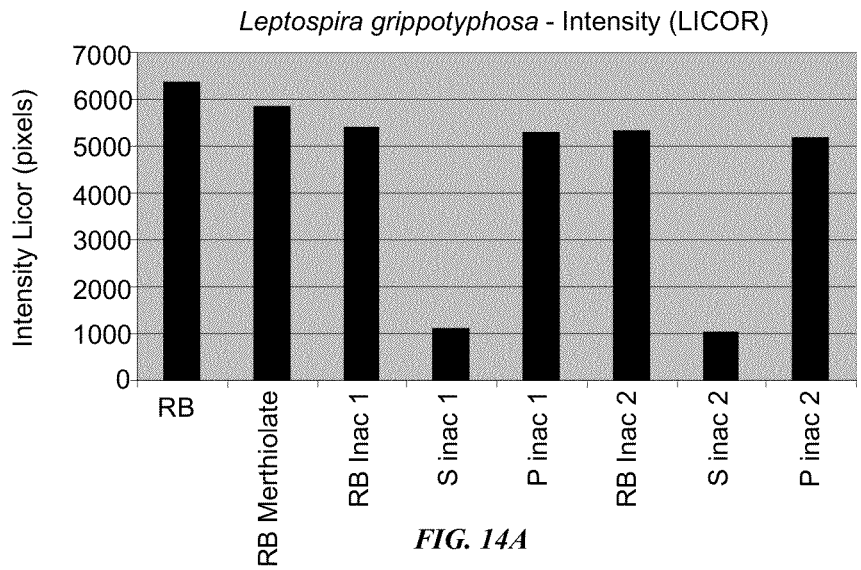
Figure 14B:
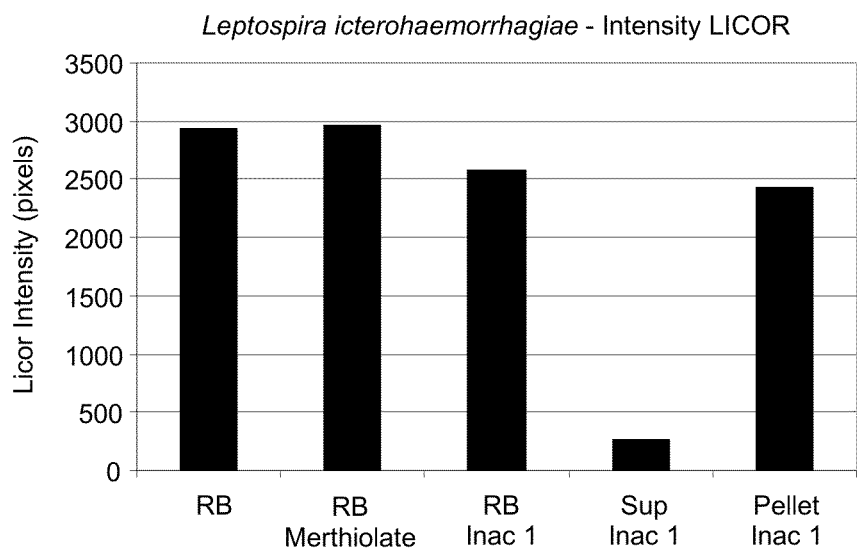
Figure 15:
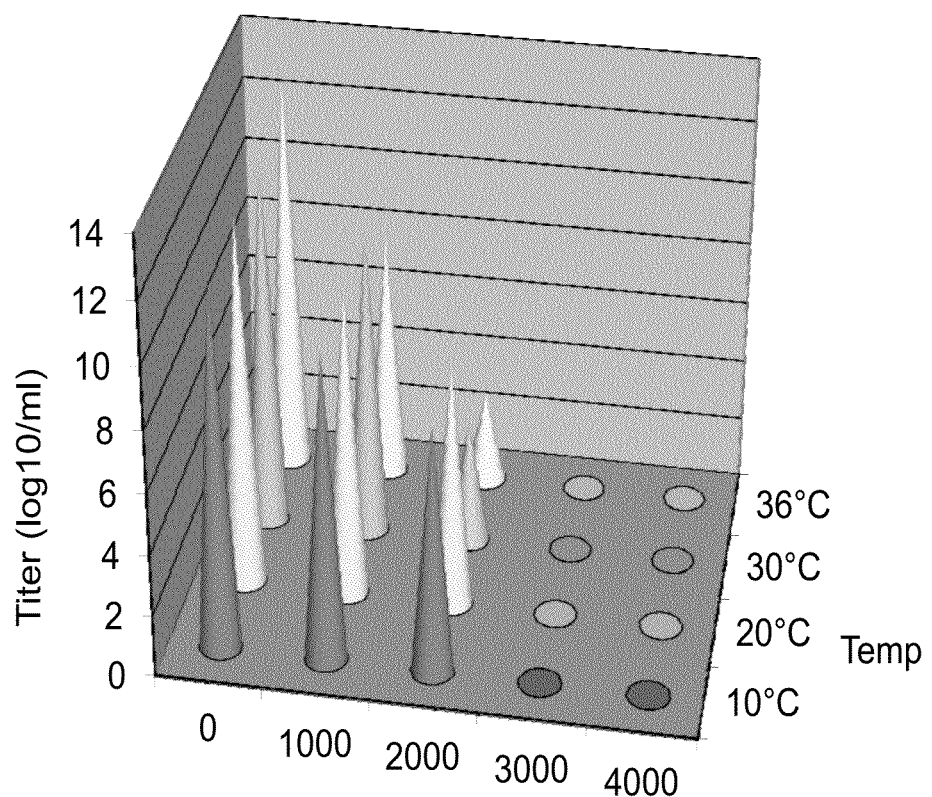
Figure 17:
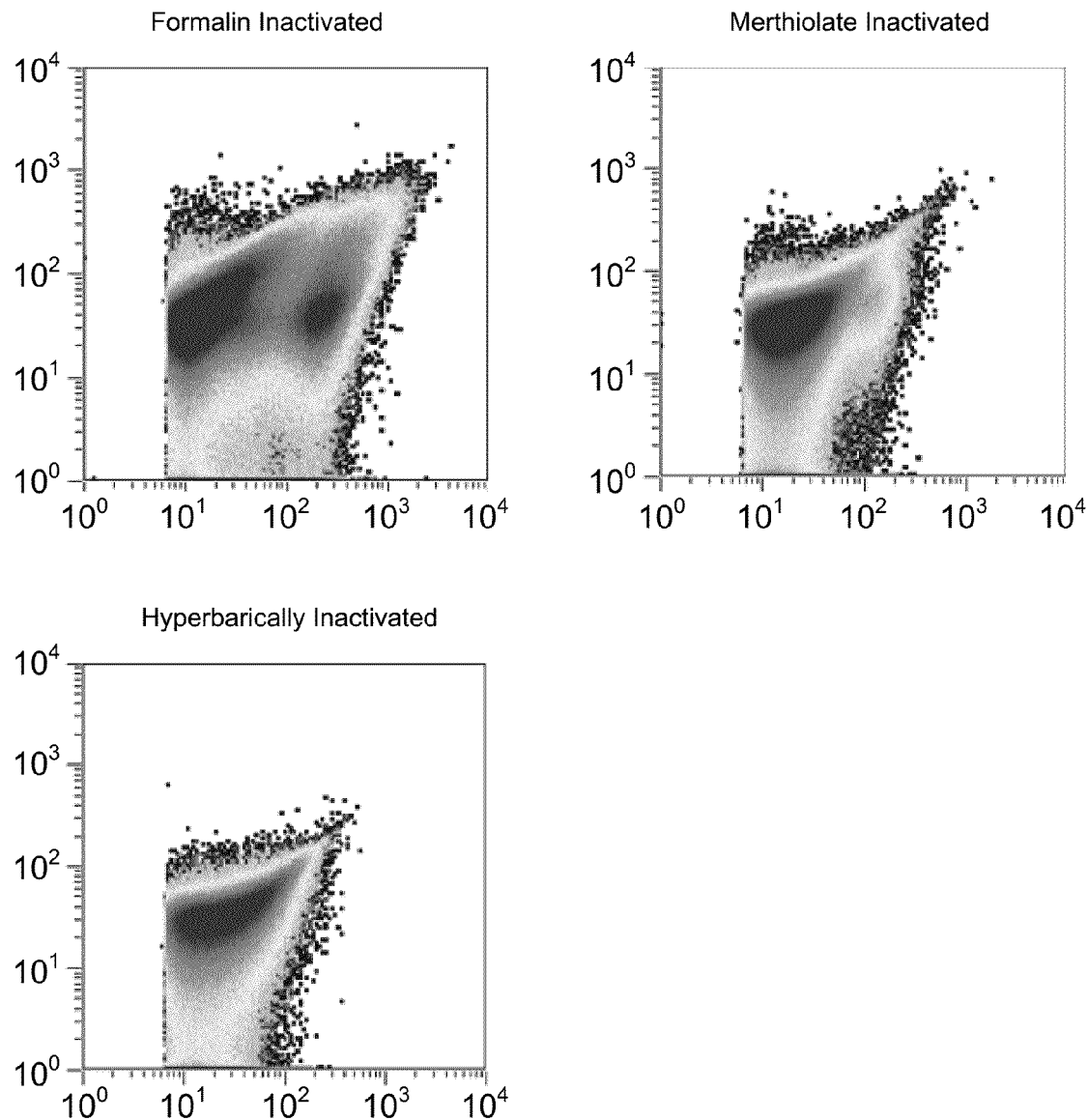

Antigens LigB and LigA (FIGS. 11 and 13) were recognized by the polyclonal antibodies for all three treatments. Hyperbaric inactivation does not alter the antigenicity of these antigens, and supernatant partitions/pellets are unchanged for all treatments considered. Finally, results of the LPS analyses for Li and Lg are presented in the FIGS. 14A and B. LPS are recognized after hyperbaric inactivation and amounts detected are identical before and after inactivation. In conclusion, hyperbaric inactivation of *Leptospira* is efficient and does not lead to changes in their antigenicity.

EXAMPLE 4

Heat and Hyperbaric Inactivation of *Bordetella pertussis*

1) Preparation of a Concentrated *B. pertussis* Suspension

A freeze-drying sample derived from the *B. pertussis* strain provided by the biology lab of the Boston Public Health Department (Massachusetts—USA) (Ref 214873M1) was taken up in Verwey medium (J. Bacteriol. 1949; 58:127-34) and used to seed a Bordet-gengou solid medium supplemented with 25% defibrinated sheep blood. After incubation (72 hours at 36° C.), bacteria were then transferred into a Verwey liquid medium supplemented with 1 g/l of ultra-filtrated autolytic yeast extract (Ref: springer 0701) and cultivated at 36° C. for about 24 hours. The bacteria were then transferred into a bioreactor filled with 4.51 of a Cohen Wheeler medium (American Journal of Public health, 1946, 36, 371-376) supplemented with 1 g/l of ultra-filtrated autolytic yeast extract, initial pH=7.3 and cultivated at 35° C. with pO2 set point at 26%. When the optical density of the cell suspension reached 0.4 at 650 nm, a fraction of this culture was used to inoculate a second bioreactor. This production bioreactor is filled with 4.5 of a Cohen Wheeler medium supplemented with 1 g/l of ultra-filtrated autolytic yeast extract. This culture is incubated at 35° C., with a dissolved oxygen set point at 26%, initial pH at 7.3 and stopped around 20 hours post-inoculation. The cell suspension was concentrated by 1) centrifugation of the culture volume at about 21 000 g for about 30 min at +5° C. and 2) resuspension of the cell pellet in an about 14 fold reduced volume of culture supernatant.

2) Heat Treatment of the Concentrated *B. pertussis* Suspension

The heat treatment of the concentrated cell suspension in culture supernatant was performed in a water bath having a temperature monitoring system that monitors the temperature parameter settings such that the temperature of the water bath was stepwise increased between 38° C. and 50° C. for a 15 minute time period, followed by a 30 minute time period where the temperature was maintained between 50° C. and 54° C., and finally a 15 minute time period where the temperature was stepwise decreased from 50° C. to 38° C.

The viability of the concentrated cell suspension was assessed before and after heat treatment by spreading 0.5 ml aliquots on 3 Petri dishes containing Bordet-gengou solid medium (Merck; Ref AX029167) supplemented with 25% sheep blood (BioMerieux; Ref: 55822). The bacteria were counted after incubation of the petri dishes at 36.5° C. for 5 days (Table 4).

TABLE 4

Viability of concentrated *B. pertussis* suspensions, before and after heat treatment.

| | Number of colonies (in CFU/ml) |
|---|---|
| 14 fold concentrated cell suspension | $6.5 \times 10^{10}$ |
| 14 fold concentrated and heat treated cell suspension | $1.4 \times 10^{6}$ |

Other temperature parameter settings relating to the time periods dedicating to the stepwise increase and stepwise decrease of the temperature between 38° C. and 50° C., in particular for time periods varying between 5 minutes and 30 minutes were also assessed. These variations were shown to have no influence on the inactivation process.

3) Hyperbaric Treatment of the Heat-Treated Concentrate of *B. pertussis*

Different conditions of hyperbaric treatment were tested: 2000 bars for 30 minutes, 3000 bars for 30 or 90 minutes, 4000 bars for 30 or 90 minutes and 5000 bars for 30 and 90 minutes. Some conditions were repeated several times.

The viability of the concentrated cell suspension was controlled after hyperbaric treatment using the same protocol as described in the previous paragraph. The results are displayed in Table 5.

TABLE 5

*B. pertussis* residual viability after various hyperbaric treatment conditions.

| Pressure (in bars) | Time (in minutes) | Residual Viability |
|---|---|---|
| 2000 | 30 | + |
| 3000 | 30 | +/− |
| 3000 | 90 | − |
| 4000 | 30 | − |
| 4000 | 90 | − |
| 5000 | 30 | − |
| 5000 | 90 | − |

+: residual bacterial growth was observed at least on one of the 3 Petri dishes used for the control of cell growth
+/−: residual bacterial growth was sometimes observed at least on one of the 3 Petri dishes used for the control of cell growth when the same hyperbaric conditions were repeated
−: no residual bacterial growth was observed on the 3 Petri dishes used for the control of cell growth.

These results show that the heat and hyperbaric-treated concentrates were fully inactivated (no residual bacterial growth) when a hyperbaric treatment of 3000 bar for more than 30 minutes was applied. When a hyperbaric treatment higher than 3000 bar was applied (for instance 4000 bar or 5000 bar), a 30 minute time period, or less was enough to fully inactivate the heat and hyperbaric-treated concentrates.

The heat and hyperbaric-treated concentrates that were fully inactivated were also tested in a "recovery test". This test was used to assess whether the inactivation results observed just after the hyperbaric treatment step were confirmed after a resting period of 15 days. The heat and hyperbaric-treated concentrates that were found inactivated were stored at room temperature for 15 days. 3 samples of 0.5 ml were then withdrawn from the concentrates and plated on 3 petri dishes containing Bordet-gengou solid medium supplemented with 25% sheep Blood. The petri dishes were incubated for 6 days at 36.5° C. and controlled for the presence of colonies. No colonies were detected, which means that there was no recovery phenomenon since no more viable bacteria were observed in the fully inactivated concentrates tested, in particular in the heat and hyperbaric-treated concentrate that was subjected to 4000 bars for 90 minutes.

4) Characterization of the Heat and Hyperbaric-Inactivated Concentrate of *B. pertussis*

The biological and analytical features of the heat and hyperbaric-inactivated concentrate, in particular the cell concentrate subjected to 4000 bars for 90 minutes were compared to those of a merthiolate-inactivated concentrate of *B. pertussis* commonly used as monovalent bulk to manufacture the whole cell pertussis vaccine. The concentrate of *B. pertussis* which was inactivated by merthiolate treatment was prepared according to the protocol described in paragraph 1).

4.1) Scanning Electron Microscopy

The morphological features of the heat and hyperbaric-inactivated concentrate and the merthiolate-inactivated concentrate as a control were examined by scanning electron microscopy (SEM). Cell concentrates were fixed in 2.5% glutaraldehyde in PBS followed by post fixation in 1% aqueous osmium tetroxide. The materials were then dehydrated in ethanol and then in hexamethyldisilizane. The two samples were then set down on mica plates for subsequent observation by SEM (Hitachi S4700, 8 KV) at different magnifications. Electron microscopy pictures (×30000 magnification) of the heat and hyperbaric-inactivated concentrate subjected to 4000 bars for 90 minutes (right side) and merthiolate-inactivated concentrate (left side) are displayed in fig . . . . No significant variations of morphology were observed between the two samples that originated from the two inactivation processes. In particular, no bacterial lysis or deformation of the bacterial cell wall was observed in the sample that originated from the heat and hyperbaric-inactivated concentrate.

4.2) Potency of the Heat and Hyperbaric-Inactivated Concentrate

The potency of the heat and hyperbaric-inactivated concentrate subjected to 4000 bars for 90 minutes was assessed by the determination of the dose that protected 50% of mice (ED 50) against the effects of a lethal dose of a *Bordetella pertussis* strain administered intra-cerebrally. This dose was compared to the ED 50 of a reference Pertussis vaccine calibrated in International Units. The potency test was carried out according to the WHO recommendations mentioned in WHO TRS n°941. The results obtained were satisfactory, which means that the association of heat treatment and hyperbaric treatments does not lower the potency of the inactivated preparation.

4.3) Specific Toxicity

The toxicity of the heat and hyperbaric treated concentrate subjected to 4000 bars for 90 minutes was tested for toxicity using the mouse weight gain test according to the recommendations of the WHO mentioned in WHO TRS n°941. The results obtained were satisfactory with no sign of toxicity.

4.4) Endotoxin Content Whole cell pertussis vaccine contains lipo-oligosaccharide endotoxins that are quantified by the *limulus amebocyte* lysate assay. The endotoxin content of the heat and hyperbaric-inactivated concentrate was within the same order of magnitude of the endotoxin content in the merthiolate-inactivated concentrate of *B. pertussis*.

EXAMPLE 4

Solubilization of KSAC Protein Expressed in *E. coli* Inclusion Bodies

KSAC (see applications arising from U.S. Ser. No. 61/694, 968) inclusion bodies were prepared in the following three buffers: 1) Tris 20 mM, 50 mM DTT, pH8; 2) Tris 20 mM, 50 mM DTT, pH8, urea 1M; 3) Tris 20 mM, 50 mM DTT, pH8, urea 2M. The KSAC inclusion bodies prepared in the same buffers at room temperature without pressure during the entire treatment duration were used as controls.

Figure 25:
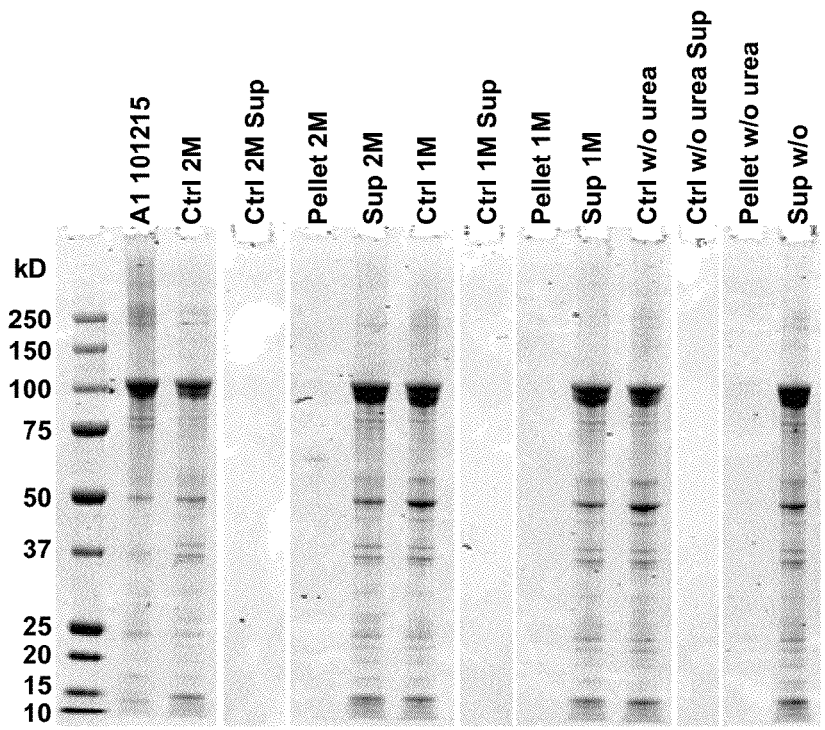
Figure 26:
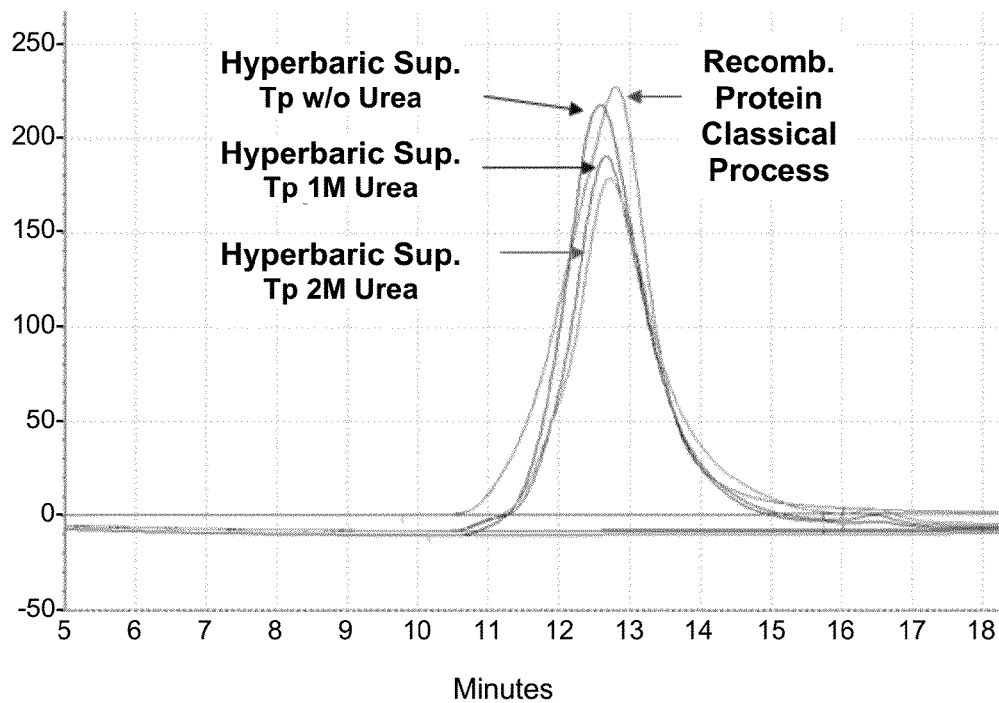

Pressurization at the target pressure was applied for 48 hours, and then the samples were depressurized for 24 hours. FIG. 25 depicts the SDS-PAGE of KSAC samples treated with 3000 bar. FIG. 26 depicts the superimposed HPLC chromatogram of the supernatant of the 3000 bar pressure treated KSAC samples and the KSAC protein obtained with the classical refolding/solubilization process. The results show that the peaks are similar and that the soluble protein obtained by high pressure treatment is organized in trimer.

TABLE 6

Quantification of KSAC protein after 3000 bar treatment by qDot-blot and HPLC.

| | control | Assay pellet | Assay supernatant |
|---|---|---|---|
| | | 2M urea | |
| Dot-blot μg/ml | 347 | 10 | 797 |
| HPLC μg/ml | — | — | 723 |
| | | 1M urea | |
| Dot-blot μg/ml | 328 | 10 | 750 |
| HPLC μg/ml | — | — | 746 |
| | | Without urea | |
| Dot-blot μg/ml | 123 | 15 | 649 |
| HPLC μg/ml | — | — | 825 |

The quantity of solubilized protein was about 800 μg/ml, which was very close to the estimated quantity of initial KSAC protein as inclusion bodies (1000 μg/ml). Yield was thus very high (75-100%).

Figure 27:
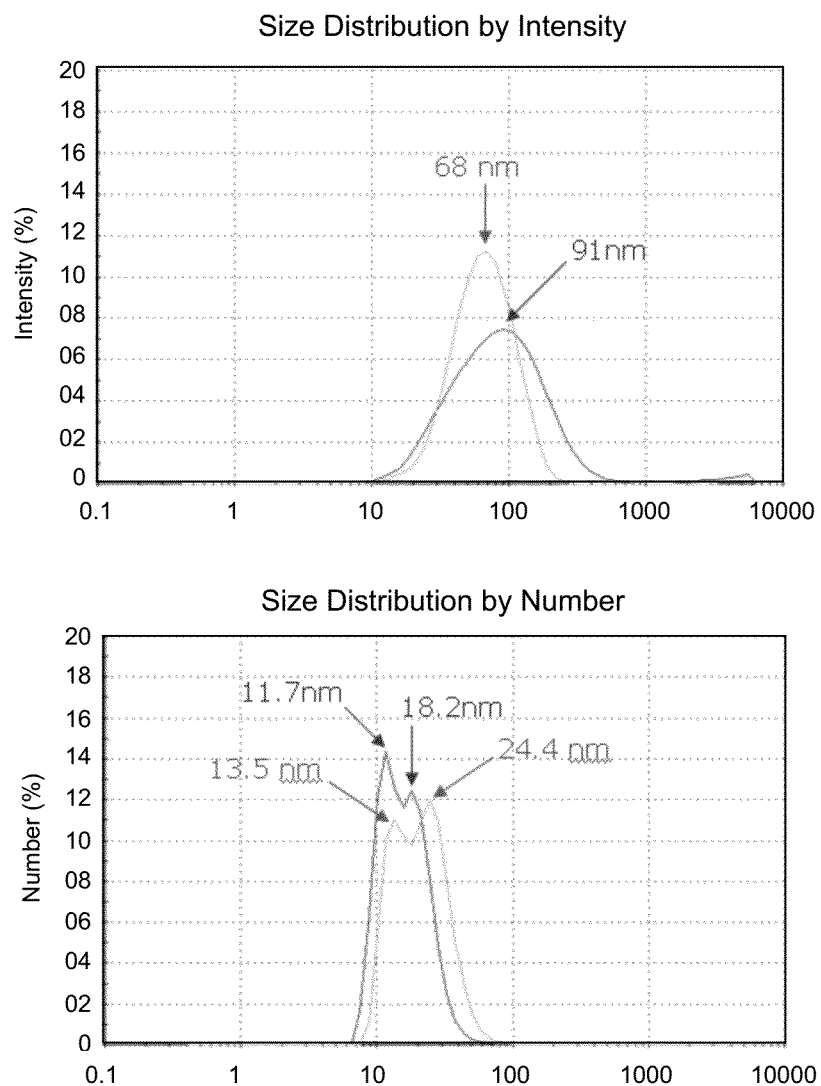
FIG. 27 shows DLS size distribution by intensity (top) and number (bottom). Shown are data for the 3000 bar pressurized protein (lighter line) and the classically refolded protein (darker line)

FIG. 27 shows the superposition of the DLS data obtained with the 3000 bar pressurized protein (lighter line) in the buffer without urea and the protein obtained with the classical refolding/solubilization process (darker line). The exhaustive range of size (upper panel) shows that less objects of larger size are detected in pressurized samples. The distribution by number (lower panel) shows that the majority of the pressure-refolded population has a similar size with the population refolded by the classical process and the folding seems very similar.

Figure 28:
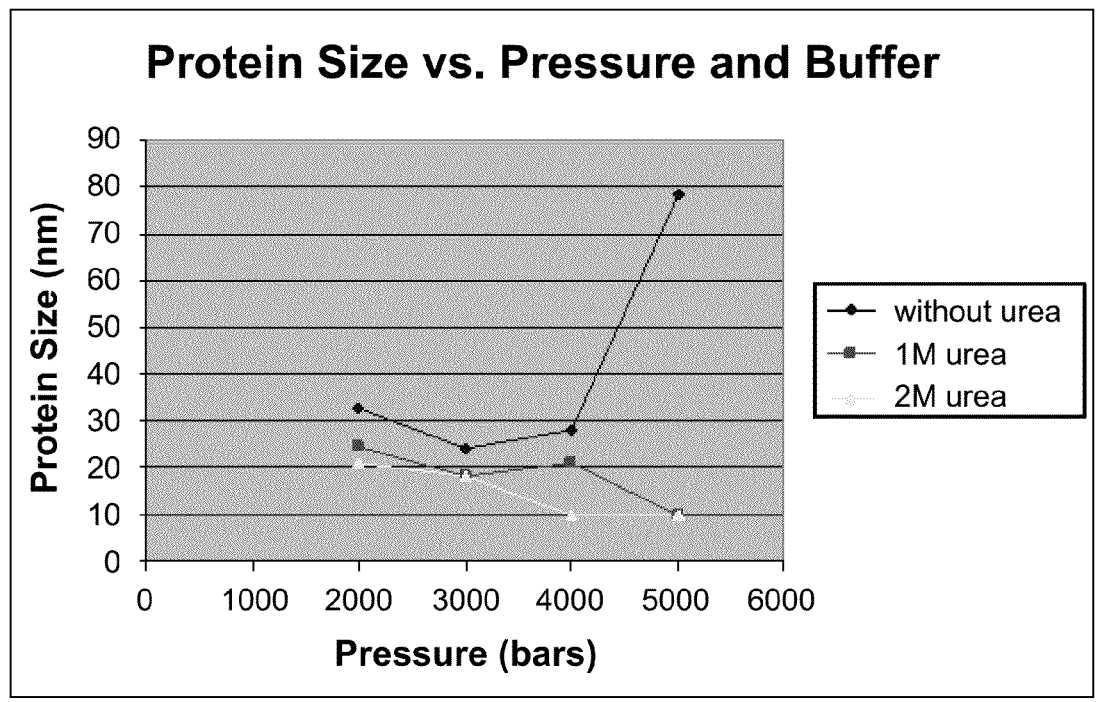
FIG. 28 shows the effect of pressure and buffer on protein size.

FIG. 28 shows that the protein sizes obtained at 3000 bar are identical to protein sizes obtained from classical chromatography refolding/solubilization for all there buffers used. When treated at 2000 bar, the protein sizes are identical to the protein sizes from classical chromatography refolding/solubilization when urea is used in the buffer. At pressure higher than 3000 bar, high-pressure aggregates appear when no urea is used. With urea present in the buffer, the protein seems to collapse (10 nm in size) which indicates that denaturation has occurred.

Figure 29:
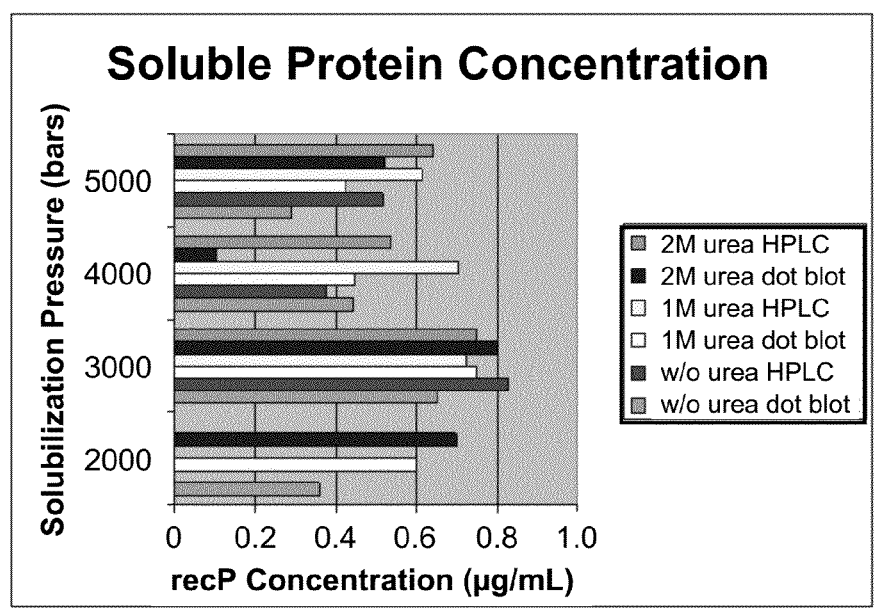
FIG. 29 shows a comparison of KSAC soluble protein content determined by HPLC & Qdot-blot.
Figure 30A:
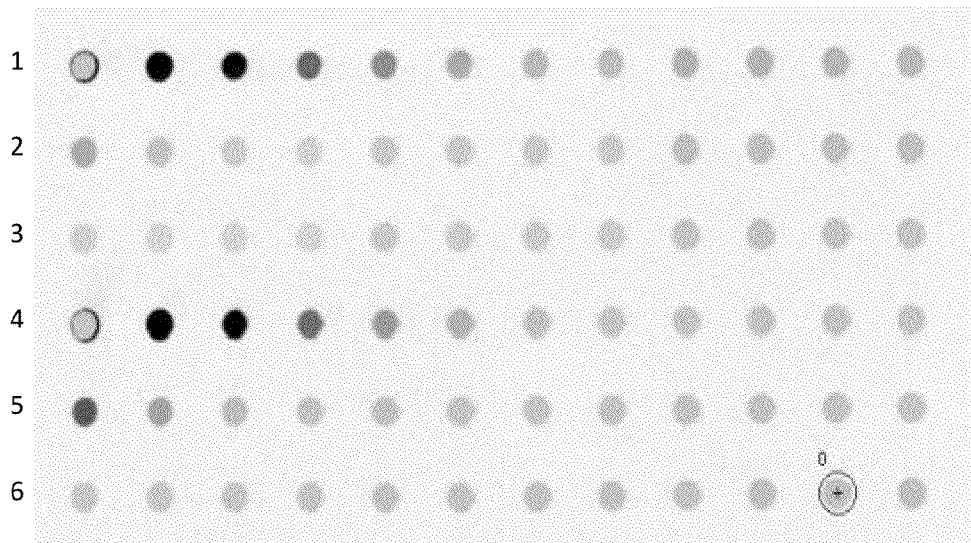
FIGS. 30A-30D depict the Q-Dot Blott analysis of KSAC samples after high pressure treatments.
Figure 30B:
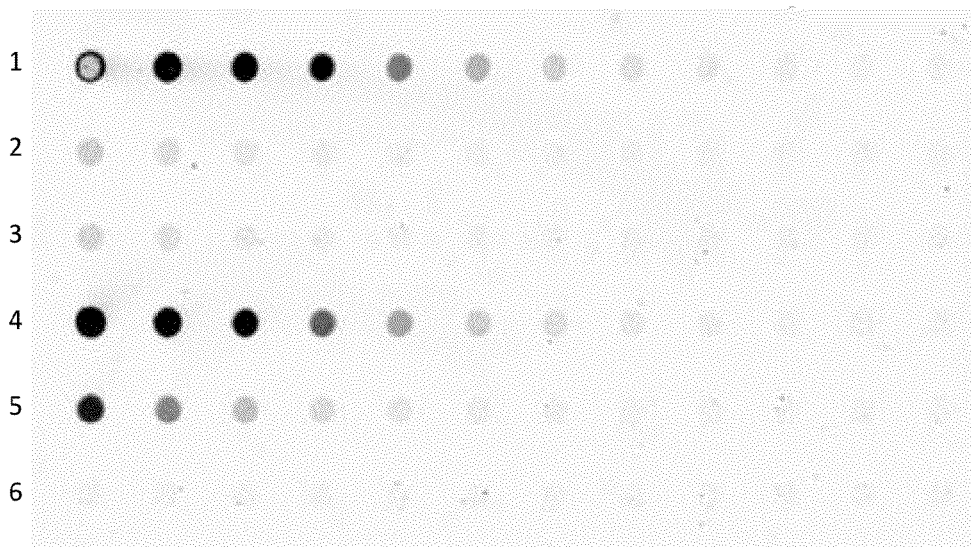
Figure 30C:
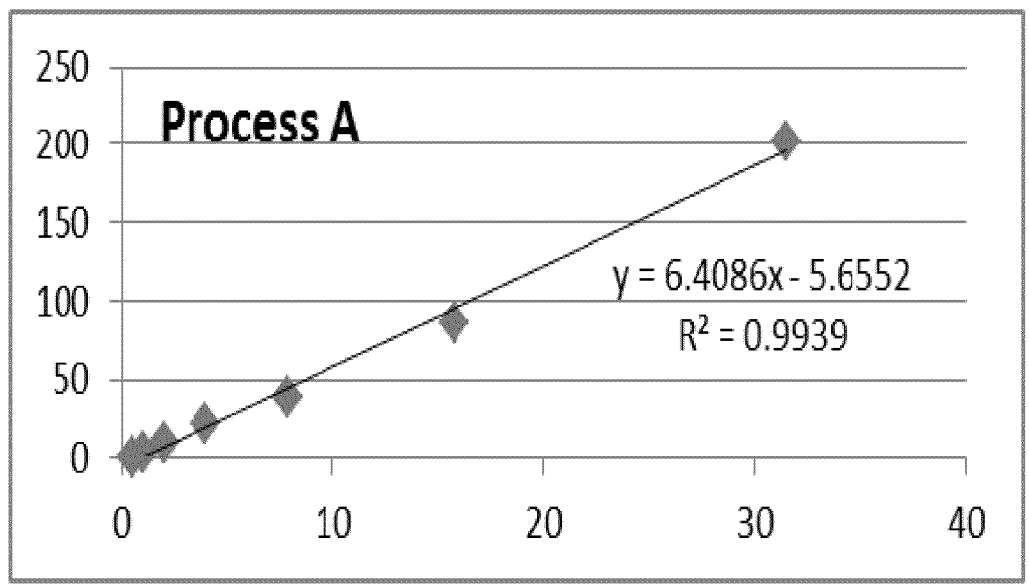
Figure 30D:
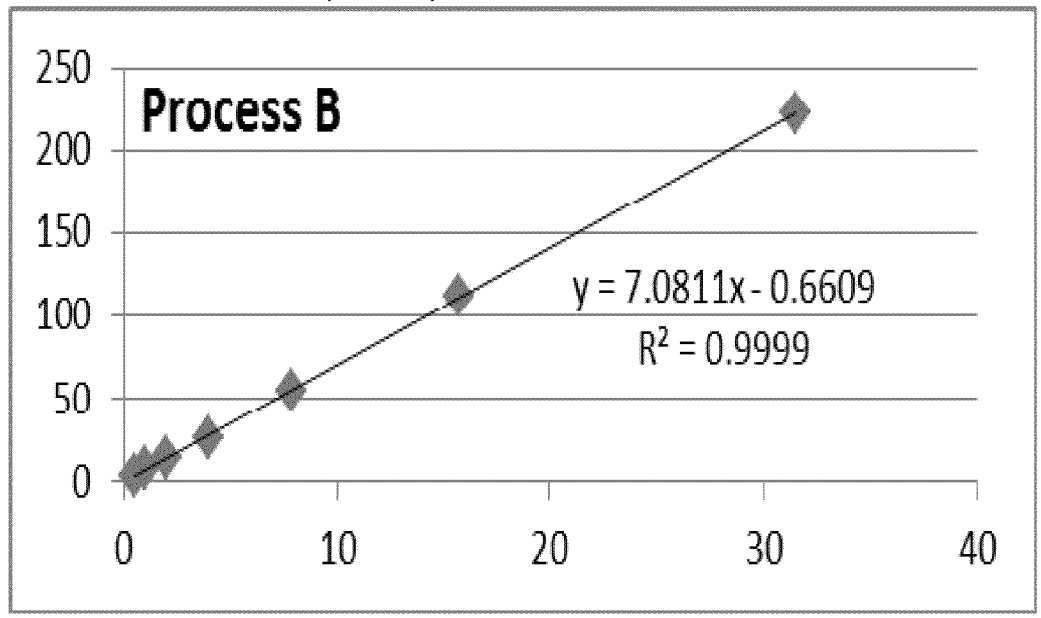
Figure 31:
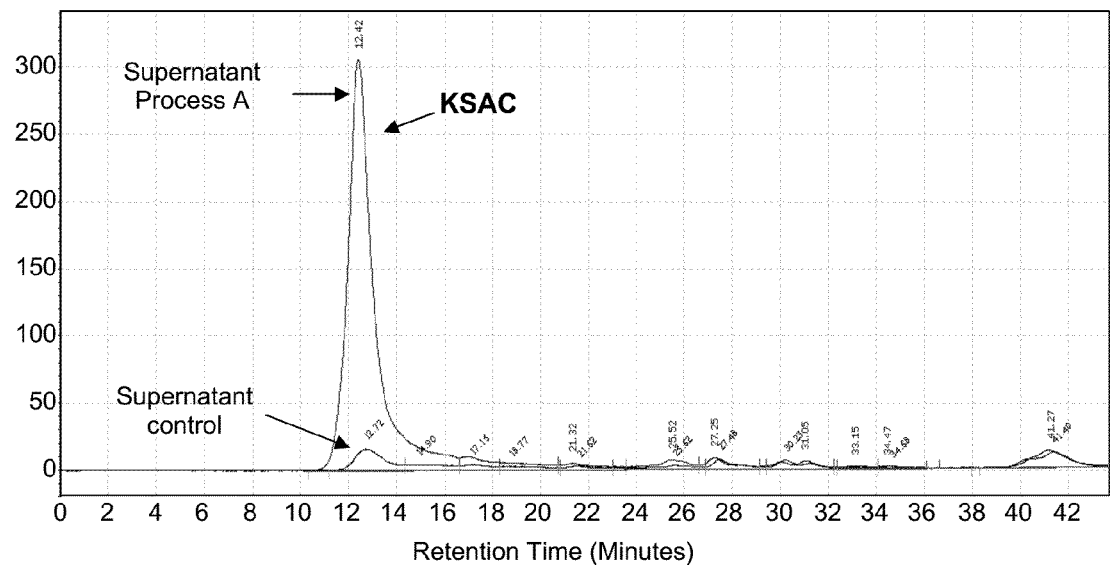
FIG. 31 depicts the HPLC analysis of KSAC samples after process A treatment.
Figure 32:
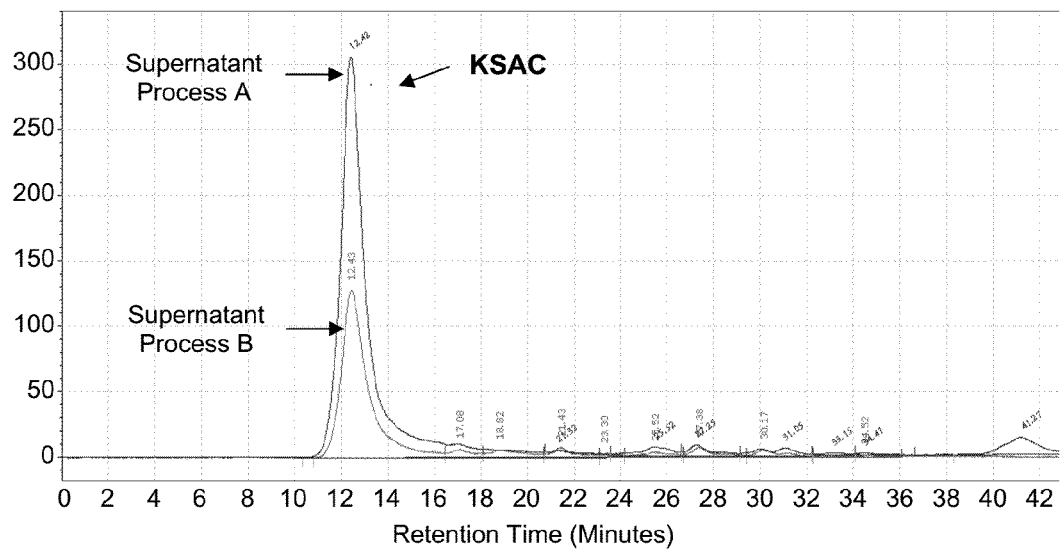
FIG. 32 depicts the HPLC analysis of KSAC samples after process B treatment.
Figure 33:
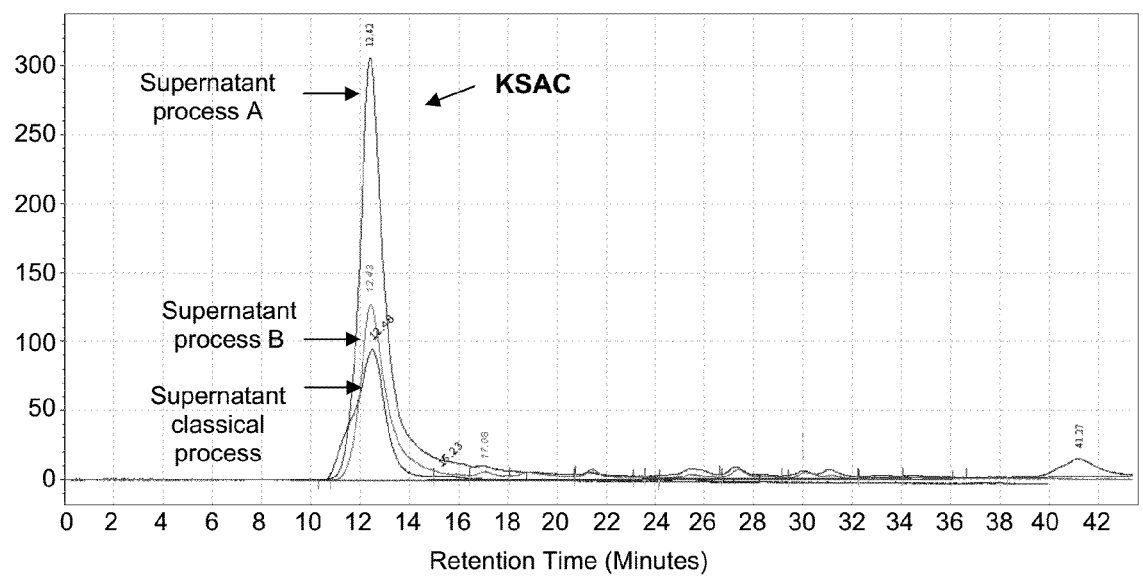
FIG. 33 depicts the HPLC analysis of KSAC samples after process A, process B and classical process treatments.

FIG. 29 shows the comparison of KSAC soluble protein content determined by HPLC and Qdot-blot. The results show that the maximum concentrations of solubilized proteins are obtained with 3000 bar treated samples with good consistency between HPLC and Qdot-blot technologies. For the 2000 bar treated samples, the presence of urea helps to increase the solubilization yield. For the 4000 bar treated samples, HPLC gives higher yield than Qdot-blot, indicating a loss of recognition of the antigens.

EXAMPLE 3

Comparison of Different Hyperbaric Solubilization Process—KSAC Protein

The objective of the study is to compare the efficiency of solubilizing protein from inclusions bodies by different processes.

The KSAC inclusion bodies produced from *E. coli* were prepared in the following buffers to form inclusion bodies suspension: a) 20 mM Tris buffer, 50 mM DiThioThreitol (DTT), pH=8.0; b) 20 mM Tris buffer, pH=8.0.

The inclusion bodies suspensions were stored in Quick Seal tubes for high pressure treatments as described below. In process A, stepwise pressurization was applied to the inclusion bodies suspensions increasing the pressure from 0 bar to 3000 bar at 1000 bar/min, with a plateau of 1 hour duration at each 500 bar (target pressure of 3000 bar reached after 5 hr). The 3000 bar pressure was maintained for 48 hours. The samples were then depressurized from 3000 bar to 0 bar at constant rate of 125 bar/hr for 24 hrs. In process B, the inclusions bodies suspensions were treated according to the method described in U.S. Pat. No. 6,489,450. The samples were subject to pressurization at constant rate up to 2500 bar in 1 hr. The 2500 bar pressure was maintained for 6 hrs. Depressurization was performed at constant rate for 1 hr reducing the pressure from 2500 bar to 0 bar. Samples were prepared as shown in Table 7 below.

TABLE 7

Inclusion bodies suspensions treatment

| Sample (1 mg/mL KSAC inclusion bodies | Buffer | High pressure treatment process |
|---|---|---|
| 1 | Tris 20 mM | Process A |
| 2 | Tris 20 mM + DTT 50 mM | Process A |
| 3 | Tris 20 mM | Control* |
| 4 | Tris 20 mM + DTT 50 mM | Control |
| 5 | Tris 20 mM | Process B |
| 6 | Tris 20 mM + DTT 50 mM | Process B |
| 7 | Tris 20 mM | Control |
| 8 | Tris 20 mM + DTT 50 mM | Control |

Control*: no high pressure treatment, stored at room temperature.

SDS-PAGE Analysis

After the high pressure treatments, the samples were centrifuged to separate the supernatant and pellets, and processed for protein analysis on SDS-PAGE. The SDS-PAGE analysis is shown in FIGS. 18A and 18B. Each well was loaded with either 5 μl of sample (crude), 5 μl of supernatant, 5 μl of pellet resuspended in Tris buffer.

The KSAC protein amounts calculated from the band intensity on the SDS-PAGE were presented in Table 8 below.

ing no DTT was used. Soluble KSAC protein was found in the supernatant of the samples treated with high pressure (both processes A and B) when buffer containing DTT was used. Surprisingly, the results of protein quantification from SAS-PAGE also indicate that process A provided better solubilization when compared to process B. This surprising result was further confirmed by the more accurate calculation of the solubilization yield for each high pressure process using Q-Dot Blot and HPLC.

Q-Dot Blot Analysis

The supernatants of the samples were analyzed by Q-Dot Blot to estimate the amount of KSAC protein solubilized by the treatments. The results are shown in FIGS. 30A-30D and Table 11.

TABLE 11

Concentrations of solubilized KSAC found in the supernatants for controls and high pressure processed samples

| Identification | Process A | Process B |
|---|---|---|
| Treatment without DTT | 26.0 g/ml | 12.7 g/ml |
| Control without DTT | 0 | 9.9 g/ml |
| Treatment with DTT | 632.1 g/ml | 368.9 g/ml |
| Control without DTT | 61.7 g/ml | 63.9 g/ml |

No significant difference was observed between the control samples (no high pressure treatment) with and without DTT. There was no soluble KSAC found in the supernatant. The Q-Dot Blot result confirmed the SDS-PAGE result.

The treatment performed using process A with DTT allowed solubilizing and refolding of the KSAC protein (detected by Q-Dot Blot). The concentration of soluble KSAC protein was found to be 632 μg/mL using process A while concentration of KSAC protein obtained using the process B was only about 369 g/mL. The solubilization yields obtained

TABLE 8

Comparative integration of the intensities of the bands measured on SDS gels

| | | Process A | | | | Process B | | | |
|---|---|---|---|---|---|---|---|---|---|
| sample | | I.I. KSAC band | Total protein I.I. | % KSAC/ total | % KSAC-S/ % KSAC-P* | I.I. KSAC band | Total protein I.I. | % KSAC/ total | % KSAC-S/ % KSAC-P |
| KSAC reference | | 36 | 49 | 73% | | 29 | 47 | 62% | |
| Control - no DTT | S[1] | 0 | 0 | 0% | — | 0 | 0 | 0% | — |
| | P[2] | 13 | 26 | 50% | | 4 | 5 | 80% | |
| | C[3] | 3 | 21 | 14% | | 6 | 16 | 38% | |
| Process - no DTT | S | 0 | 9 | 0% | 0% | 0 | 2 | 0% | 0% |
| | P | 43 | 76 | 57% | | 28 | 39 | 72% | |
| | C | 27 | 86 | 31% | | 14 | 41 | 34% | |
| Control - with DTT | S | 1 | 8 | 13% | — | 0 | 0 | 0% | — |
| | P | 20 | 40 | 50% | | 24 | 36 | 67% | |
| | C | 16 | 31 | 52% | | 22 | 37 | 59% | |
| Process - with DTT | S | 55 | 127 | 43% | 75% | 18 | 29 | 62% | 69% |
| | P | 8 | 14 | 57% | | 8 | 9 | 89% | |
| | C | 45 | 106 | 42% | | 28 | 47 | 60% | |
| KSAC reference | | 38 | 52 | 73% | | 29 | 45 | 64% | |

S[1]: supernatant
P[2]: pellet
C[3]: crude, before centrifugation
% KSAC-S/% KSAC-P*: [% KSAC/total in supernatant]/[% KSAC/total in pellet]

The results show that there is no significant amount of KSAC detected in the supernatant of the controls or the samples treated with processes A and B when buffer containare 63% for process A and 37% for process B. The Q-Dot Blot results further demonstrate that process A is more efficient in producing soluble and refolded proteins.

HPLC Analysis

FIG. 20 shows the superposition of the HPLC chromatograms of the supernatant of the control and process A treated sample. The retention time, retention volume and estimated purity obtained for the process A treated sample are show in Table 11 below.

TABLE 11

Retention time, retention volume and estimated purity obtained for process A treated sample

| Detection | Information | Control - no processing | After Process A |
|---|---|---|---|
| UV | RT (Retention time - min) | 12.7 | 12.4 |
|  | VR (Retention volume - mL) | 6.64 | 6.46 |
|  | Estimated Purity (%) | 17.3 | 85.5 |

Figure 21:
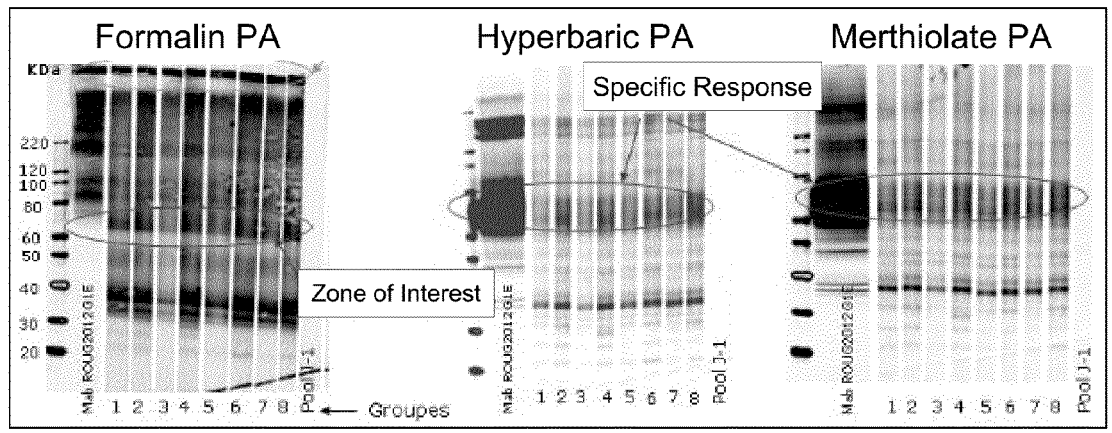

FIG. 21 shows the superposition of the HPLC chromatograms of the supernatant of process A treated sample and process B treated sample. The retention time, retention volume and estimated purity obtained for the process A treated sample are show in Table 12 below.

TABLE 12

Retention time, retention volume and estimated purity obtained for process A and B treated samples

| Detection | Information | Process A | Process B |
|---|---|---|---|
| UV | RT (Retention time - min) | 12.4 | 12.4 |
|  | VR (Retention volume - mL) | 6.46 | 6.47 |
|  | Estimated Purity (%) | 85.5 | 74.2 |

Figure 22:
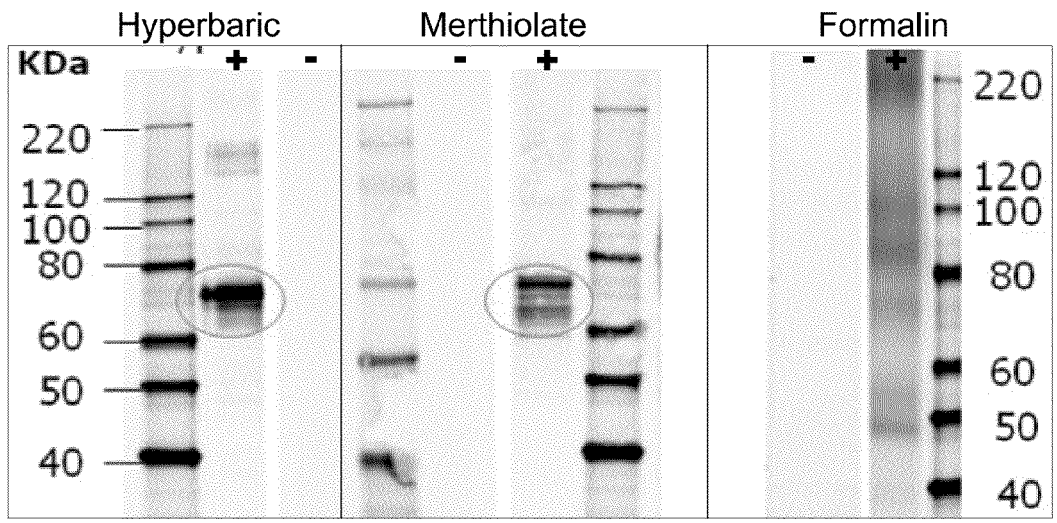

FIG. 22 shows the superposition of the HPLC chromatograms of the supernatant of process A treated sample, process B treated sample and classical process treated sample (denaturation and refolding obtained by urea and DTT treatment). The retention time, retention volume and estimated purity obtained for the process A treated sample are show in Table 13 below.

TABLE 13

Retention time, retention volume and estimated purity obtained for process A, process B and classical process treated samples

| Detection | Information | Classical process | Process A | Process B |
|---|---|---|---|---|
| UV | RT (Retention time - min) | 12.5 | 12.4 | 12.4 |
|  | VR (Retention volume - mL) | 6.50 | 6.46 | 6.47 |
|  | Peak area (mAU) | 8628 | 25251 | 10506 |
|  | Estimated purity (%) | 94.7 | 85.5 | 74.2 |

The HPLC results further confirmed that process A provided better solubilization of KSAC protein than process B judging from the peak areas (25251 mAu for process A vs. 10506 mAU for process B). Both process A and B allow obtaining a refolding of the KSAC protein very close to the one obtained using the classical process (solubilization using urea+DTT treatment and refolding by SEC chromatography). The trials performed with both processes A and B did not yield significant soluble KSAC protein in the absence of DTT. The results confirmed that a reducing agent is needed during the high pressure treatment to break disulfide bonds. However, the unexpected surprising discovery is that there is no need for the removal of DTT in order to obtain a correct refolding of the protein. Contrary to the general knowledge that DTT has to be removed from the buffer in order for proteins to be refolded properly, it is surprisingly discovered by applicants that presence of DTT does not interfere with the refolding process in the high pressure treatment of present invention. The KSAC soluble proteins obtained from high pressure process of present invention were refolded correctly to form trimmers in the presence of DTT.

REFERENCES

C. Silva et al: Effect of hydrostatic pressure on the *Leptospira interrogans*: high immunogenicity of the pressure-inactivated serovar hardjo; Vaccine 19, 2001, 1511-1514.

P. Cullen et al: Surfaceome of *Leptospira* spp.; Infection And Immunity 73, 2005, 4853-4863.

W. Yan et al: Immunogenicity and protective efficacy of recombinant *leptospira* immunoglobulin-like protein B (rLigB) in a hamster challenge model; Microbes And Infection 2, 2009, 230-237.

M. Ritz et al: Effects of high hydrostatic pressure on membrane proteins of *Salmonella typhimurium*; International Journal of Food Microbiology 55, 2000, 115-119.

N. Wilkinson et al: Resistance of poliovirus to inactivation by high hydrostatic pressures; Innovative Food Science and Emerging Technologies 2, 2001, 95-98.

Isbarn S. et al: Inactivation of avian influenza virus by heat and high hydrostatic pressure; Journal of Food Protection 70, 2007, 667-673.

Shearer and Kniel. High Hydrostatic Pressure for Development of Vaccines. Journal of Food Protection. Vol. 72, No. 7, 2009, Pages 1500-1508.

What is claimed is:

1. A hyperbaric device for inactivating microorganisms or solubilizing and refolding peptides comprising:

(a) an enclosure;

(b) at least one computer processor and a programmable user interface therefor;

(c) a means for supplying super-ambient pressure;

(d) a means for controlling the temperature and pressure of a pressure transmitting fluid;

(e) a means for decontaminating the device for routine cleaning purposes or in the event of rupture of a sample pouch; and (f) a means for receiving into the device, conveying within the device, and expelling from the device, trays or receptacles that are adapted to receive sample pouches comprising either microorganisms to be inactivated or peptides to be solubilized and refolded.

2. The device of claim 1, wherein the pressure means comprises an isostatic press comprising a piston.

3. The device of claim 2, further comprising a means to monitor the inactivation status of the microorganisms.

4. The device of claim 3, wherein the inactivation monitoring means comprises a needle or other suitable probe, which can aseptically penetrate the pouches to remove a sample of the microorganisms for subsequent viability testing.

5. The device of any one of claims 1 to 4, and substantially as depicted in FIG. 2A, comprising:

(a) a primary fluid chamber (8);

(b) a pressure intensifier chamber (9);

(c) a high pressure fluid chamber (3), which is configured to receive fluid via an inlet (2);

(d) a pressure ram/piston (5), which is capable of moving between an extended position and a retracted position;

(e) a seal (6) and a plug (7), which are configured to prevent the fluid from escaping the high pressure fluid chamber (3) when the ram (5) moves from its retracted position to its extended position;

wherein pressure is communicated from a pressure intensifier device to the pressure intensifier chamber (9), and from the pressure intensifier chamber (9) to the primary fluid chamber (8);

wherein pressure from the primary fluid chamber (8) is communicated to the high pressure fluid chamber (2) via moving the ram (s) from its retracted position to its extended position; and wherein after completion of a pressurization and depressurization cycle(s), the fluid is discharged via an outlet (4).

6. The device of claim 5, wherein
the fluid enters the high pressure fluid chamber (3) via inlet (2) while the pressure ram (5) is in its retracted position.

7. The device of claim 6, wherein the ram (5) physically blocks the fluid inlet (2) as it begins to extend, and wherein during the pressurization cycle, when the ram (s) is moving from it retracted position to its extended position, the seal (6) prevents the fluid from escaping from the high pressure fluid chamber (3) via the inlet (2); and wherein the plug (7) prevents the fluid from escaping from the high pressure chamber via outlet (4).

8. A method for hyperbarically inactivating microorganisms for the purpose of preparing the microorganisms for use as components of a vaccine composition, comprising the steps of:
(a) subjecting the microorganisms to elevated pressure for defined periods of time;
(b) determining that the microorganisms are 100% inactivated; thereby inactivating the microorganisms; and
wherein the method is performed using the device of claim 5.

9. The method of claim 8, wherein the microorganisms are subjected to more than one cycle of elevated pressure.

10. The method of claim 9, further comprising the step of evaluating the immunogenicity of the inactivated microorganisms.

11. The method of claim 10, wherein the evaluating is performed using ELISA specific for antigens known or inferred to be responsible for eliciting a protective immune response in a target animal.

12. A hyperbaric-inactivated pathogen produced using the method of claim 9.

13. The pathogen of claim 12, which is of the genus *Leptospira*.

14. The pathogen of claim 12, which is *Erysipelothrix rhusiopathiae*.

15. The method of claim 8, further comprising the step of monitoring the inactivation status of the microorganisms as a function of time via an automatic viability testing means.

16. A method for hyperbarically inactivating a cell suspension of *Bordetella pertussis*, comprising the steps of:
(a) producing a cell suspension of *Bordetella pertussis* in a culture medium,
(b) concentrating the cell suspension produced in said culture medium, optionally supplemented with saline (0.9% NaCl) or a buffer solution that does not exceed 25% of the final volume (V/V),
(c) heating the concentrated cell suspension at a temperature between 50° C. to 54° C. (limits included), and (d) inactivating the heat-treated and concentrated cell suspension by high pressure treatment wherein the pressure is higher than about 2000 bars but lower than about 6000 bars; and
wherein the method is performed using the device of claim 5.

17. The method of claim 16, wherein the culture medium is the Cohen Wheeler medium.

18. The method of claim 16, wherein the heating at a temperature between 50° C. to 54° C. (limits included) lasts about 30 minutes.

19. The method of claim 16, wherein the pressure is between about 3000 bars and about 5000 bars.

20. A process for manufacturing a whole cell *pertussis* vaccine comprising the steps of:
(a) using the method of any one of claims 16 to 19 to inactivate a concentrated cell suspension of *Bordetella pertussis;*
(b) diluting the inactivated concentrated cell suspension of *B. pertussis* in a pharmaceutically acceptable excipient, thereby manufacturing the whole cell *pertussis* vaccine.

21. A hyperbaric-inactivated pathogen produced using the device of claim 5.

22. The pathogen of claim 21, which is of the genus *Leptospira*.

23. The pathogen of claim 21, which is *Erysipelothrix rhusiopathiae*.

24. An immunogenic composition comprising the inactivated pathogen of claim 21.

25. The composition of claim 24, which is a vaccine composition, capable of eliciting in an animal a protective immune response against a living, virulent form of the inactivated pathogen.

26. The composition of claim 24, further comprising a pharmaceutically or veterinarily acceptable vehicle or carrier, and optionally an adjuvant.

27. A method of manufacturing a vaccine composition comprising the step of mixing the pathogen of claim 24, with an appropriate vehicle or carrier, and optionally an adjuvant, thereby manufacturing the vaccine composition.

28. The method of claim 27, wherein the adjuvant is a mucosal adjuvant.

29. A method of producing a soluble protein expressed in prokaryotes or eukaryotes comprising the steps of:
(a) preparing the *E. coli* inclusion bodies in a buffer containing no or low concentration of urea to form inclusion body suspension; and
(b) subjecting the inclusion body suspension to a high pressure, thereby producing the soluble protein; and
wherein the method is performed using the device of claim 5.

30. The method of claim 29, wherein the buffer further comprises DTT.

31. The method of claim 30, wherein the DTT concentration is from about 1 mM to about 100 mM.

32. The method of claim 29, wherein the high pressure is in the range from about 2000 bar to about 5000 bar.

33. The method of claim 29, wherein the inclusion bodies are subject to the high pressure for about 20 hours to about 100 hours.

34. The method of claim 29, wherein the urea concentration is from 0 M to about 7 M.

35. The method of claim 29, wherein the method further comprises the step of depressurization.

36. A method of producing a soluble protein expressed in prokaryotes or eukaryotes comprising the steps of:

(a) preparing the inclusion bodies in a buffer containing no or low concentration of urea to form inclusion body suspension;
(b) subjecting the inclusion body suspension to a stepwise increase of pressure over a period of time; and
(c) maintaining the high pressure applied to the inclusion bodies for a period of time, thereby producing the soluble protein; and
wherein the method is performed using the device of claim 5.

37. A composition comprising a protein refolded by the hyperbaric device of claim 1.

38. The composition of claim 37, wherein the protein was subjected to high pressure of from about 1000 bar to about 5000 bar.

39. The composition of claim 38, wherein the high pressure was applied for at least 20 hours.

40. The composition of claim 38, wherein protein was solubilized or refolded from *E. coli* inclusion bodies.

41. The composition of claim 40, wherein the *E. coli* inclusion bodies were prepared in a buffer containing no or low urea.

42. The composition of claim 41, wherein the *E. coli* inclusion bodies were further subjected to a high pressure ranging from about 1000 bar to about 5000 bar.

43. The composition of claim 40, wherein the *E. coli* inclusion bodies were prepared in a buffer containing DTT.

44. The composition of claim 40, wherein the *E. coli* inclusion bodies were treated under the high pressure for about 20 hours to about 100 hours.

45. The composition of claim 40, wherein the *E. coli* inclusion bodies were depressurized at around 83 bar/min-125 bar/min.

* * * * *